United States Patent
Rogers et al.

(10) Patent No.: US 11,219,412 B2
(45) Date of Patent: Jan. 11, 2022

(54) IN-EAR HEALTH MONITORING

(71) Applicant: Google LLC, Mountain View, CA (US)

(72) Inventors: Jeffrey L. Rogers, San Carlos, CA (US); Brian Derek DeBusschere, Los Gatos, CA (US)

(73) Assignee: Google LLC, Mountain View, CA (US)

( * ) Notice: Subject to any disclaimer, the term of this patent is extended or adjusted under 35 U.S.C. 154(b) by 369 days.

(21) Appl. No.: 15/976,518

(22) Filed: May 10, 2018

(65) Prior Publication Data
US 2018/0256106 A1 Sep. 13, 2018

Related U.S. Application Data

(63) Continuation of application No. 14/666,155, filed on Mar. 23, 2015, now Pat. No. 10,016,162.

(51) Int. Cl.
*A61B 5/01* (2006.01)
*A61B 5/00* (2006.01)
(Continued)

(52) U.S. Cl.
CPC .......... *A61B 5/6817* (2013.01); *A61B 5/0008* (2013.01); *A61B 5/0022* (2013.01);
(Continued)

(58) Field of Classification Search
CPC ... A61B 5/6817; A61B 5/6898; A61B 5/0008; A61B 5/0022; A61B 5/7221; A61B 5/01; A61B 5/7405; A61B 5/4836; A61B 5/7246; A61B 2562/0271; A61F 7/12; G01J 5/0011; G01J 5/0025; G01J 5/021;
(Continued)

(56) References Cited

U.S. PATENT DOCUMENTS 3,570,312 A * 3/1971 Kreith ...................... A61B 5/01
374/183
3,610,874 A 10/1971 Gagliano
(Continued)

FOREIGN PATENT DOCUMENTS

CN 103355860 1/2016
DE 102011075725 11/2012
(Continued)

OTHER PUBLICATIONS

Hollington, J. "Playing Back All Songs on iPod" <https://www.ilounge.com/index.php/articles/comments/playing-back-all-songs-on-ipod> (Year: 2008).*
(Continued)

*Primary Examiner* — David J. McCrosky
(74) *Attorney, Agent, or Firm* — Colby Nipper PLLC

(57) ABSTRACT

This document describes techniques for, and systems that enable, in-ear health monitoring. The techniques described herein enable early detection of health conditions (e.g., contagious disease) through use of an in-ear health-monitoring and audio device. These techniques prompt a user, often through the user's smart phone, to listen to audio content through the device, which also takes the user's temperature. Through repetitive use, the techniques are capable of determining a temperature differential for the user, which aids in early detection of a contagious disease or other malady.

20 Claims, 7 Drawing Sheets

(51) Int. Cl.
*A61F 7/12* (2006.01)
*G01J 5/04* (2006.01)
*G01J 5/00* (2006.01)
*G01K 7/22* (2006.01)
*G16H 50/80* (2018.01)
*G01J 5/06* (2006.01)
*G06Q 50/22* (2018.01)

(52) U.S. Cl.
CPC ............ *A61B 5/01* (2013.01); *A61B 5/6898* (2013.01); *A61B 5/7221* (2013.01); *A61B 5/7246* (2013.01); *A61B 5/7405* (2013.01); *A61F 7/12* (2013.01); *G01J 5/0011* (2013.01); *G01J 5/049* (2013.01); *G01K 7/22* (2013.01); *A61B 2562/0271* (2013.01); *G01J 2005/063* (2013.01); *G01J 2005/067* (2013.01); *G06Q 50/22* (2013.01); *G16H 50/80* (2018.01)

(58) Field of Classification Search
CPC ...... G01J 5/04; G01J 5/049; G01J 5/06; G01J 2005/062; G01J 2005/063; G01J 2005/067; G01J 2005/068; G01J 5/0818; G16H 50/00–80
See application file for complete search history.

(56) References Cited

U.S. PATENT DOCUMENTS

| | | |
|---|---|---|
| 3,953,706 A | 4/1976 | Harris et al. |
| 4,321,930 A | 3/1982 | Jobsis et al. |
| 4,654,967 A | 4/1987 | Thenner |
| 4,700,044 A | 10/1987 | Hokanson et al. |
| 4,795,998 A | 1/1989 | Dunbar et al. |
| 4,838,797 A | 6/1989 | Dodier |
| 5,024,533 A * | 6/1991 | Egawa ............... G01J 5/02 374/126 |
| 5,121,124 A | 6/1992 | Spivey et al. |
| 5,298,715 A | 3/1994 | Chalco et al. |
| 5,309,916 A | 5/1994 | Hatschek |
| 5,341,979 A | 8/1994 | Gupta |
| 5,410,471 A | 4/1995 | Alyfuku et al. |
| 5,468,917 A | 11/1995 | Brodsky et al. |
| 5,564,571 A | 10/1996 | Zanotti |
| 5,656,798 A | 8/1997 | Kubo et al. |
| 5,724,707 A | 3/1998 | Kirk et al. |
| 5,798,798 A | 8/1998 | Rector et al. |
| 6,032,450 A | 3/2000 | Blum |
| 6,037,893 A | 3/2000 | Lipman |
| 6,080,690 A | 6/2000 | Lebby et al. |
| 6,129,673 A * | 10/2000 | Fraden ............... G01J 5/04 374/E13.003 |
| 6,179,785 B1 * | 1/2001 | Martinosky ............... G01J 5/02 374/E13.003 |
| 6,210,771 B1 | 4/2001 | Post et al. |
| 6,254,544 B1 | 7/2001 | Hayashi |
| 6,313,825 B1 | 11/2001 | Gilbert |
| 6,340,979 B1 | 1/2002 | Beaton et al. |
| 6,386,757 B1 | 5/2002 | Konno |
| 6,440,593 B2 | 8/2002 | Ellison et al. |
| 6,492,980 B2 | 12/2002 | Sandbach |
| 6,493,933 B1 | 12/2002 | Post et al. |
| 6,513,970 B1 | 2/2003 | Tabata et al. |
| 6,524,239 B1 | 2/2003 | Reed et al. |
| 6,543,668 B1 | 4/2003 | Fujii et al. |
| 6,616,613 B1 | 9/2003 | Goodman |
| 6,711,354 B2 | 3/2004 | Kameyama |
| 6,717,065 B2 | 4/2004 | Hosaka et al. |
| 6,802,720 B2 | 10/2004 | Weiss et al. |
| 6,805,672 B2 * | 10/2004 | Martin ............... A61B 5/01 600/504 |
| 6,835,898 B2 | 12/2004 | Eldridge et al. |
| 6,854,985 B1 | 2/2005 | Weiss |
| 6,929,484 B2 | 8/2005 | Weiss et al. |
| 6,970,128 B1 | 11/2005 | Dwelly et al. |
| 6,997,882 B1 | 2/2006 | Parker et al. |
| 7,134,879 B2 | 11/2006 | Sugimoto et al. |
| 7,164,820 B2 | 1/2007 | Eves et al. |
| 7,194,371 B1 | 3/2007 | McBride et al. |
| 7,209,775 B2 * | 4/2007 | Bae ............... A61B 5/0002 374/E13.003 |
| 7,223,105 B2 | 5/2007 | Weiss et al. |
| 7,249,954 B2 | 7/2007 | Weiss |
| 7,299,964 B2 | 11/2007 | Jayaraman et al. |
| 7,310,236 B2 | 12/2007 | Takahashi et al. |
| 7,317,416 B2 | 1/2008 | Flom et al. |
| 7,348,285 B2 | 3/2008 | Dhawan et al. |
| 7,365,031 B2 | 4/2008 | Swallow et al. |
| 7,421,061 B2 | 9/2008 | Boese et al. |
| 7,462,035 B2 | 12/2008 | Lee et al. |
| 7,528,082 B2 | 5/2009 | Krans et al. |
| 7,544,627 B2 | 6/2009 | Tao et al. |
| 7,578,195 B2 | 8/2009 | DeAngelis et al. |
| 7,644,488 B2 | 1/2010 | Aisenbrey |
| 7,647,093 B2 | 1/2010 | Bojovic et al. |
| 7,670,144 B2 | 3/2010 | Ito et al. |
| 7,677,729 B2 | 3/2010 | Vilser et al. |
| 7,691,067 B2 | 4/2010 | Westbrook et al. |
| 7,698,154 B2 | 4/2010 | Marchosky |
| 7,791,700 B2 | 9/2010 | Bellamy |
| 7,834,276 B2 | 11/2010 | Chou et al. |
| 7,952,512 B1 | 5/2011 | Delker et al. |
| 7,999,722 B2 | 8/2011 | Beeri et al. |
| 8,062,220 B2 | 11/2011 | Kurtz et al. |
| 8,169,404 B1 | 5/2012 | Boillot |
| 8,179,604 B1 | 5/2012 | Prada Gomez et al. |
| 8,193,929 B1 | 6/2012 | Siu et al. |
| 8,199,104 B2 | 6/2012 | Park et al. |
| 8,282,232 B2 | 10/2012 | Hsu et al. |
| 8,289,185 B2 | 10/2012 | Alonso |
| 8,301,232 B2 | 10/2012 | Albert et al. |
| 8,334,226 B2 | 12/2012 | Nhan et al. |
| 8,341,762 B2 | 1/2013 | Balzano |
| 8,367,942 B2 | 2/2013 | Howell et al. |
| 8,374,668 B1 * | 2/2013 | Hayter ............... A61B 5/14532 600/347 |
| 8,475,367 B1 | 7/2013 | Yuen et al. |
| 8,505,474 B2 | 8/2013 | Kang et al. |
| 8,509,882 B2 | 8/2013 | Albert et al. |
| 8,549,829 B2 | 10/2013 | Song et al. |
| 8,560,972 B2 | 10/2013 | Wilson |
| 8,562,526 B2 | 10/2013 | Heneghan et al. |
| 8,569,189 B2 | 10/2013 | Bhattacharya et al. |
| 8,614,689 B2 | 12/2013 | Nishikawa et al. |
| 8,655,004 B2 | 2/2014 | Prest et al. |
| 8,700,137 B2 | 4/2014 | Albert |
| 8,758,020 B2 | 6/2014 | Burdea et al. |
| 8,759,713 B2 | 6/2014 | Sheats |
| 8,764,651 B2 | 7/2014 | Tran |
| 8,785,778 B2 | 7/2014 | Streeter et al. |
| 8,790,257 B2 | 7/2014 | Libbus et al. |
| 8,814,574 B2 | 8/2014 | Selby et al. |
| 8,819,812 B1 | 8/2014 | Weber et al. |
| 8,854,433 B1 | 10/2014 | Rafii |
| 8,926,509 B2 * | 1/2015 | Magar ............... H04W 52/0235 600/301 |
| 9,055,879 B2 | 6/2015 | Selby et al. |
| 9,075,429 B1 | 7/2015 | Karakotsios et al. |
| 9,093,289 B2 | 7/2015 | Vicard et al. |
| 9,125,456 B2 | 9/2015 | Chow |
| 9,141,194 B1 | 9/2015 | Keyes et al. |
| 9,148,949 B2 | 9/2015 | Guofu et al. |
| 9,230,160 B1 | 1/2016 | Kanter |
| 9,331,422 B2 | 5/2016 | Nazzaro et al. |
| 9,335,825 B2 | 5/2016 | Rautiainen et al. |
| 9,508,141 B2 | 11/2016 | Khachaturian et al. |
| 9,575,560 B2 | 2/2017 | Poupyrev et al. |
| 9,588,625 B2 | 3/2017 | Poupyrev |
| 9,594,443 B2 | 3/2017 | VanBlon et al. |
| 9,600,080 B2 | 3/2017 | Poupyrev |
| 9,693,592 B2 | 7/2017 | Robinson et al. |
| 9,729,986 B2 * | 8/2017 | Crawley ............... H04R 29/001 |
| 9,778,749 B2 | 10/2017 | Poupyrev |

(56) References Cited

U.S. PATENT DOCUMENTS

| | | |
|---|---|---|
| 9,811,164 B2 | 11/2017 | Poupyrev |
| 9,837,760 B2 | 12/2017 | Karagozler et al. |
| 9,848,780 B1 | 12/2017 | DeBusschere et al. |
| 9,921,660 B2 | 3/2018 | Poupyrev |
| 9,933,908 B2 | 4/2018 | Poupyrev |
| 10,016,162 B1 | 7/2018 | Rogers et al. |
| 10,064,582 B2 | 9/2018 | Rogers |
| 10,080,528 B2 | 9/2018 | Debusschere et al. |
| 10,304,567 B2 * | 5/2019 | Kitagawa ............... G16H 50/30 |
| 10,376,195 B1 | 8/2019 | Reid et al. |
| 10,409,385 B2 | 9/2019 | Poupyrev |
| 10,642,367 B2 | 5/2020 | Poupyrev |
| 10,664,059 B2 | 5/2020 | Poupyrev |
| 10,936,081 B2 | 3/2021 | Poupyrev |
| 11,169,988 B2 | 11/2021 | Poupyrev et al. |
| 2002/0080156 A1 | 6/2002 | Abbott et al. |
| 2002/0170897 A1 | 11/2002 | Hall |
| 2003/0036685 A1 | 2/2003 | Goodman |
| 2003/0071750 A1 | 4/2003 | Benitz |
| 2003/0093000 A1 | 5/2003 | Nishio et al. |
| 2003/0100228 A1 | 5/2003 | Bungo et al. |
| 2003/0119391 A1 | 6/2003 | Swallow et al. |
| 2003/0122677 A1 | 7/2003 | Kail |
| 2004/0009729 A1 | 1/2004 | Hill et al. |
| 2004/0102693 A1 | 5/2004 | Jenkins |
| 2004/0249250 A1 | 12/2004 | McGee et al. |
| 2004/0259391 A1 | 12/2004 | Jung et al. |
| 2005/0069695 A1 | 3/2005 | Jung et al. |
| 2005/0128124 A1 | 6/2005 | Greneker et al. |
| 2005/0148876 A1 | 7/2005 | Endoh et al. |
| 2006/0035554 A1 | 2/2006 | Glaser et al. |
| 2006/0040739 A1 | 2/2006 | Wells |
| 2006/0100517 A1 | 5/2006 | Phillips |
| 2006/0139314 A1 | 6/2006 | Bell |
| 2006/0157734 A1 | 7/2006 | Onodero et al. |
| 2006/0166620 A1 | 7/2006 | Sorensen |
| 2006/0183980 A1 * | 8/2006 | Yang ...................... G16H 20/70 |
| | | 600/301 |
| 2006/0258205 A1 | 11/2006 | Locher et al. |
| 2007/0024946 A1 | 2/2007 | Panasyuk et al. |
| 2007/0026695 A1 | 2/2007 | Lee et al. |
| 2007/0118043 A1 | 5/2007 | Oliver et al. |
| 2007/0161921 A1 | 7/2007 | Rausch |
| 2007/0176821 A1 | 8/2007 | Flom et al. |
| 2007/0192647 A1 | 8/2007 | Glaser |
| 2007/0197115 A1 | 8/2007 | Eves et al. |
| 2007/0197878 A1 | 8/2007 | Shklarski |
| 2007/0210074 A1 | 9/2007 | Maurer et al. |
| 2007/0276262 A1 | 11/2007 | Banet et al. |
| 2007/0276632 A1 | 11/2007 | Banet et al. |
| 2008/0001735 A1 | 1/2008 | Tran |
| 2008/0002027 A1 | 1/2008 | Kondo et al. |
| 2008/0015422 A1 | 1/2008 | Wessel |
| 2008/0024438 A1 | 1/2008 | Collins et al. |
| 2008/0039731 A1 | 2/2008 | McCombie et al. |
| 2008/0065291 A1 | 3/2008 | Breed |
| 2008/0134102 A1 | 6/2008 | Movold et al. |
| 2008/0136775 A1 | 6/2008 | Conant |
| 2008/0168396 A1 | 7/2008 | Matas et al. |
| 2008/0194975 A1 | 8/2008 | MacQuarrie et al. |
| 2008/0211766 A1 | 9/2008 | Westerman et al. |
| 2008/0233822 A1 | 9/2008 | Swallow et al. |
| 2008/0278450 A1 | 11/2008 | Lashina |
| 2008/0282665 A1 | 11/2008 | Speleers |
| 2008/0291158 A1 | 11/2008 | Park et al. |
| 2008/0303800 A1 | 12/2008 | Elwell |
| 2008/0316085 A1 | 12/2008 | Rofougaran et al. |
| 2008/0320419 A1 | 12/2008 | Matas et al. |
| 2009/0018408 A1 | 1/2009 | Ouchi et al. |
| 2009/0033585 A1 | 2/2009 | Lang |
| 2009/0053950 A1 | 2/2009 | Surve |
| 2009/0056300 A1 | 3/2009 | Chung et al. |
| 2009/0058820 A1 | 3/2009 | Hinckley |
| 2009/0113298 A1 | 4/2009 | Jung et al. |
| 2009/0115617 A1 | 5/2009 | Sano et al. |
| 2009/0118648 A1 | 5/2009 | Kandori et al. |
| 2009/0149036 A1 | 6/2009 | Lee et al. |
| 2009/0177068 A1 | 7/2009 | Stivoric et al. |
| 2009/0203244 A1 | 8/2009 | Toonder |
| 2009/0253585 A1 | 10/2009 | Diatchenko et al. |
| 2009/0270690 A1 | 10/2009 | Roos et al. |
| 2009/0288762 A1 | 11/2009 | Wolfel |
| 2009/0295712 A1 | 12/2009 | Ritzau |
| 2009/0299197 A1 | 12/2009 | Antonelli et al. |
| 2009/0319181 A1 | 12/2009 | Khosravy et al. |
| 2010/0045513 A1 | 2/2010 | Pett et al. |
| 2010/0060570 A1 | 3/2010 | Underkoffler et al. |
| 2010/0065320 A1 | 3/2010 | Urano |
| 2010/0069730 A1 | 3/2010 | Bergstrom et al. |
| 2010/0071205 A1 | 3/2010 | Graumann et al. |
| 2010/0094141 A1 | 4/2010 | Puswella |
| 2010/0179820 A1 | 7/2010 | Harrison et al. |
| 2010/0201586 A1 | 8/2010 | Michalk |
| 2010/0204550 A1 | 8/2010 | Heneghan et al. |
| 2010/0205667 A1 | 8/2010 | Anderson et al. |
| 2010/0208035 A1 | 8/2010 | Pinault et al. |
| 2010/0225562 A1 | 9/2010 | Smith |
| 2010/0241009 A1 | 9/2010 | Petkie |
| 2010/0281438 A1 | 11/2010 | Latta et al. |
| 2010/0292549 A1 | 11/2010 | Schuler |
| 2010/0306713 A1 | 12/2010 | Geisner et al. |
| 2010/0313414 A1 | 12/2010 | Sheats |
| 2010/0324384 A1 | 12/2010 | Moon et al. |
| 2010/0325770 A1 | 12/2010 | Chung et al. |
| 2011/0003664 A1 | 1/2011 | Richard |
| 2011/0010014 A1 | 1/2011 | Oexman et al. |
| 2011/0018795 A1 | 1/2011 | Jang |
| 2011/0029038 A1 | 2/2011 | Hyde et al. |
| 2011/0073353 A1 | 3/2011 | Lee et al. |
| 2011/0093820 A1 | 4/2011 | Zhang et al. |
| 2011/0118564 A1 | 5/2011 | Sankai |
| 2011/0119640 A1 | 5/2011 | Berkes et al. |
| 2011/0166940 A1 | 7/2011 | Bangera et al. |
| 2011/0181509 A1 | 7/2011 | Rautiainen et al. |
| 2011/0181510 A1 | 7/2011 | Hakala et al. |
| 2011/0193939 A1 | 8/2011 | Vassigh et al. |
| 2011/0197263 A1 | 8/2011 | Stinson, III |
| 2011/0202404 A1 | 8/2011 | van der Riet |
| 2011/0213218 A1 | 9/2011 | Weiner et al. |
| 2011/0221666 A1 | 9/2011 | Newton et al. |
| 2011/0234492 A1 | 9/2011 | Ajmera et al. |
| 2011/0239118 A1 | 9/2011 | Yamaoka et al. |
| 2011/0245688 A1 | 10/2011 | Arora et al. |
| 2011/0279303 A1 | 11/2011 | Smith |
| 2011/0303341 A1 | 12/2011 | Meiss et al. |
| 2011/0307842 A1 | 12/2011 | Chiang et al. |
| 2011/0318985 A1 | 12/2011 | McDermid |
| 2012/0001875 A1 | 1/2012 | Li et al. |
| 2012/0019168 A1 | 1/2012 | Noda et al. |
| 2012/0029369 A1 | 2/2012 | Icove et al. |
| 2012/0047468 A1 | 2/2012 | Santos et al. |
| 2012/0068876 A1 | 3/2012 | Bangera et al. |
| 2012/0092284 A1 | 4/2012 | Rogougaran et al. |
| 2012/0105358 A1 | 5/2012 | Momeyer et al. |
| 2012/0123232 A1 | 5/2012 | Najarian et al. |
| 2012/0127082 A1 | 5/2012 | Kushler et al. |
| 2012/0144934 A1 | 6/2012 | Russell et al. |
| 2012/0150493 A1 | 6/2012 | Casey et al. |
| 2012/0156926 A1 | 6/2012 | Kato et al. |
| 2012/0174299 A1 | 7/2012 | Balzano |
| 2012/0174736 A1 | 7/2012 | Wang et al. |
| 2012/0193801 A1 | 8/2012 | Gross et al. |
| 2012/0220835 A1 | 8/2012 | Chung |
| 2012/0248093 A1 | 10/2012 | Ulrich et al. |
| 2012/0254810 A1 | 10/2012 | Heck et al. |
| 2012/0268416 A1 | 10/2012 | Pirogov et al. |
| 2012/0270564 A1 | 10/2012 | Gum et al. |
| 2012/0280900 A1 | 11/2012 | Wang et al. |
| 2012/0310665 A1 | 12/2012 | Xu et al. |
| 2013/0016070 A1 | 1/2013 | Starner et al. |
| 2013/0035563 A1 | 2/2013 | Angellides |
| 2013/0046544 A1 | 2/2013 | Kay et al. |
| 2013/0053653 A1 | 2/2013 | Cuddihy et al. |
| 2013/0076788 A1 | 3/2013 | Ben Zvi |

(56) References Cited

U.S. PATENT DOCUMENTS

| | | |
|---|---|---|
| 2013/0079649 A1 | 3/2013 | Mestha et al. |
| 2013/0082922 A1 | 4/2013 | Miller |
| 2013/0083173 A1 | 4/2013 | Geisner et al. |
| 2013/0086533 A1 | 4/2013 | Stienstra |
| 2013/0096439 A1 | 4/2013 | Lee et al. |
| 2013/0102217 A1 | 4/2013 | Jeon |
| 2013/0104084 A1 | 4/2013 | Mlyniec et al. |
| 2013/0106710 A1 | 5/2013 | Ashbrook |
| 2013/0113830 A1 | 5/2013 | Suzuki |
| 2013/0132931 A1 | 5/2013 | Bruns et al. |
| 2013/0147833 A1 | 6/2013 | Aubauer et al. |
| 2013/0150735 A1 | 6/2013 | Cheng |
| 2013/0161078 A1 | 6/2013 | Li |
| 2013/0194173 A1 | 8/2013 | Zhu et al. |
| 2013/0195330 A1 | 8/2013 | Kim et al. |
| 2013/0196716 A1 | 8/2013 | Khurram |
| 2013/0207962 A1 | 8/2013 | Oberdorfer et al. |
| 2013/0222232 A1 | 8/2013 | Kong et al. |
| 2013/0260630 A1 | 10/2013 | Ito et al. |
| 2013/0278499 A1 | 10/2013 | Anderson |
| 2013/0278501 A1 | 10/2013 | Bulzacki |
| 2013/0283203 A1 | 10/2013 | Batraski et al. |
| 2013/0310700 A1 | 11/2013 | Wiard et al. |
| 2013/0322729 A1 | 12/2013 | Mestha et al. |
| 2013/0332438 A1 | 12/2013 | Li et al. |
| 2013/0345569 A1 | 12/2013 | Mestha et al. |
| 2014/0005809 A1 | 1/2014 | Frei et al. |
| 2014/0049487 A1 | 2/2014 | Konertz et al. |
| 2014/0051941 A1 | 2/2014 | Messerschmidt |
| 2014/0070957 A1 | 3/2014 | Longinotti-Buitoni et al. |
| 2014/0072190 A1 | 3/2014 | Wu et al. |
| 2014/0073486 A1 | 3/2014 | Ahmed et al. |
| 2014/0073969 A1 | 3/2014 | Zou et al. |
| 2014/0081100 A1 | 3/2014 | Muhsin et al. |
| 2014/0095480 A1 | 4/2014 | Marantz et al. |
| 2014/0121540 A1 | 5/2014 | Raskin |
| 2014/0135631 A1 | 5/2014 | Brumback et al. |
| 2014/0139422 A1 | 5/2014 | Mistry et al. |
| 2014/0139616 A1 | 5/2014 | Pinter et al. |
| 2014/0143678 A1 | 5/2014 | Mistry et al. |
| 2014/0181509 A1 | 6/2014 | Liu |
| 2014/0184496 A1 | 7/2014 | Gribetz et al. |
| 2014/0188989 A1 | 7/2014 | Stekkelpak et al. |
| 2014/0191939 A1 | 7/2014 | Penn et al. |
| 2014/0200416 A1 | 7/2014 | Kashef et al. |
| 2014/0208275 A1 | 7/2014 | Mongia et al. |
| 2014/0215389 A1 | 7/2014 | Walsh et al. |
| 2014/0239065 A1 | 8/2014 | Zhou et al. |
| 2014/0244277 A1 | 8/2014 | Krishna Rao et al. |
| 2014/0246415 A1 | 9/2014 | Wittkowski |
| 2014/0247212 A1 | 9/2014 | Kim et al. |
| 2014/0250515 A1 | 9/2014 | Jakobsson |
| 2014/0253431 A1 | 9/2014 | Gossweiler et al. |
| 2014/0253709 A1 | 9/2014 | Bresch et al. |
| 2014/0262478 A1 | 9/2014 | Harris et al. |
| 2014/0265642 A1* | 9/2014 | Utley ................. H02J 7/35 307/151 |
| 2014/0275854 A1 | 9/2014 | Venkatraman et al. |
| 2014/0276104 A1 | 9/2014 | Tao et al. |
| 2014/0280295 A1 | 9/2014 | Kurochikin et al. |
| 2014/0281975 A1 | 9/2014 | Anderson |
| 2014/0297006 A1 | 10/2014 | Sadhu |
| 2014/0306936 A1 | 10/2014 | Dahl et al. |
| 2014/0316261 A1 | 10/2014 | Lux et al. |
| 2014/0318699 A1 | 10/2014 | Longinotti-Buitoni et al. |
| 2014/0324888 A1 | 10/2014 | Xie et al. |
| 2014/0343392 A1 | 11/2014 | Yang |
| 2014/0347295 A1 | 11/2014 | Kim et al. |
| 2014/0357369 A1 | 12/2014 | Callens et al. |
| 2014/0368378 A1 | 12/2014 | Crain et al. |
| 2014/0376788 A1 | 12/2014 | Xu et al. |
| 2015/0002391 A1 | 1/2015 | Chen |
| 2015/0009096 A1 | 1/2015 | Lee et al. |
| 2015/0026815 A1 | 1/2015 | Barrett |
| 2015/0029050 A1 | 1/2015 | Driscoll et al. |
| 2015/0030256 A1 | 1/2015 | Brady et al. |
| 2015/0040040 A1 | 2/2015 | Balan et al. |
| 2015/0046183 A1 | 2/2015 | Cireddu |
| 2015/0068069 A1 | 3/2015 | Tran et al. |
| 2015/0077282 A1 | 3/2015 | Mohamadi |
| 2015/0085060 A1 | 3/2015 | Fish et al. |
| 2015/0091858 A1 | 4/2015 | Rosenberg et al. |
| 2015/0091859 A1 | 4/2015 | Rosenberg et al. |
| 2015/0091903 A1 | 4/2015 | Costello et al. |
| 2015/0095987 A1 | 4/2015 | Potash et al. |
| 2015/0099941 A1 | 4/2015 | Tran |
| 2015/0100328 A1 | 4/2015 | Kress et al. |
| 2015/0112606 A1 | 4/2015 | He et al. |
| 2015/0133017 A1 | 5/2015 | Liao et al. |
| 2015/0143601 A1 | 5/2015 | Longinotti-Buitoni et al. |
| 2015/0145805 A1 | 5/2015 | Liu |
| 2015/0162729 A1 | 6/2015 | Reversat et al. |
| 2015/0177866 A1 | 6/2015 | Hwang et al. |
| 2015/0199045 A1 | 7/2015 | Robucci et al. |
| 2015/0205358 A1 | 7/2015 | Lyren |
| 2015/0256763 A1 | 9/2015 | Niemi |
| 2015/0257653 A1 | 9/2015 | Hyde et al. |
| 2015/0261320 A1 | 9/2015 | Leto |
| 2015/0268027 A1 | 9/2015 | Gerdes |
| 2015/0268799 A1 | 9/2015 | Starner et al. |
| 2015/0277569 A1 | 10/2015 | Sprenger et al. |
| 2015/0280102 A1 | 10/2015 | Tajitsu et al. |
| 2015/0287187 A1 | 10/2015 | Redtel |
| 2015/0297105 A1 | 10/2015 | Pahlevan et al. |
| 2015/0301167 A1 | 10/2015 | Sentelle et al. |
| 2015/0312041 A1 | 10/2015 | Choi |
| 2015/0332075 A1 | 11/2015 | Burch |
| 2015/0346701 A1 | 12/2015 | Gordon et al. |
| 2015/0346820 A1 | 12/2015 | Poupyrev et al. |
| 2015/0351703 A1 | 12/2015 | Phillips et al. |
| 2015/0375339 A1 | 12/2015 | Sterling et al. |
| 2016/0011668 A1 | 1/2016 | Gilad-Bachrach et al. |
| 2016/0018948 A1 | 1/2016 | Parvarandeh et al. |
| 2016/0026253 A1 | 1/2016 | Bradski et al. |
| 2016/0026768 A1* | 1/2016 | Singh ................. G01K 1/20 705/3 |
| 2016/0038083 A1 | 2/2016 | Ding et al. |
| 2016/0041617 A1 | 2/2016 | Poupyrev |
| 2016/0041618 A1 | 2/2016 | Poupyrev |
| 2016/0045706 A1 | 2/2016 | Gary et al. |
| 2016/0048235 A1 | 2/2016 | Poupyrev |
| 2016/0048236 A1 | 2/2016 | Poupyrev |
| 2016/0054792 A1 | 2/2016 | Poupyrev |
| 2016/0054803 A1 | 2/2016 | Poupyrev |
| 2016/0054804 A1 | 2/2016 | Gollakata et al. |
| 2016/0055201 A1 | 2/2016 | Poupyrev et al. |
| 2016/0089042 A1 | 3/2016 | Saponas et al. |
| 2016/0098089 A1 | 4/2016 | Poupyrev |
| 2016/0100166 A1 | 4/2016 | Dragne et al. |
| 2016/0103500 A1 | 4/2016 | Hussey et al. |
| 2016/0106328 A1 | 4/2016 | Mestha et al. |
| 2016/0145776 A1 | 5/2016 | Roh |
| 2016/0186366 A1 | 6/2016 | McMaster |
| 2016/0206244 A1 | 7/2016 | Rogers |
| 2016/0213331 A1 | 7/2016 | Gil et al. |
| 2016/0216825 A1 | 7/2016 | Forutanpour |
| 2016/0220152 A1 | 8/2016 | Meriheina et al. |
| 2016/0249698 A1 | 9/2016 | Berzowska et al. |
| 2016/0252965 A1 | 9/2016 | Mandella et al. |
| 2016/0253044 A1 | 9/2016 | Katz |
| 2016/0259037 A1 | 9/2016 | Molchanov et al. |
| 2016/0282988 A1 | 9/2016 | Poupyrev |
| 2016/0283101 A1 | 9/2016 | Schwesig et al. |
| 2016/0284436 A1 | 9/2016 | Fukuhara et al. |
| 2016/0287172 A1 | 10/2016 | Morris et al. |
| 2016/0299526 A1 | 10/2016 | Inagaki et al. |
| 2016/0320852 A1 | 11/2016 | Poupyrev |
| 2016/0320853 A1 | 11/2016 | Lien et al. |
| 2016/0320854 A1 | 11/2016 | Lien et al. |
| 2016/0321428 A1 | 11/2016 | Rogers |
| 2016/0338599 A1 | 11/2016 | DeBusschere et al. |
| 2016/0345638 A1 | 12/2016 | Robinson et al. |
| 2016/0349790 A1 | 12/2016 | Connor |
| 2016/0349845 A1 | 12/2016 | Poupyrev et al. |

(56) References Cited

U.S. PATENT DOCUMENTS

| | | |
|---|---|---|
| 2017/0013417 A1 | 1/2017 | Zampini, II |
| 2017/0060298 A1 | 3/2017 | Hwang et al. |
| 2017/0075496 A1 | 3/2017 | Rosenberg et al. |
| 2017/0097413 A1 | 4/2017 | Gillian et al. |
| 2017/0097684 A1 | 4/2017 | Lien |
| 2017/0115777 A1 | 4/2017 | Poupyrev |
| 2017/0125940 A1 | 5/2017 | Karagozler et al. |
| 2017/0164904 A1 | 6/2017 | Kirenko |
| 2017/0192523 A1 | 7/2017 | Poupyrev |
| 2017/0192629 A1 | 7/2017 | Takada et al. |
| 2017/0196513 A1 | 7/2017 | Longinotti-Buitoni et al. |
| 2017/0232538 A1 | 8/2017 | Robinson et al. |
| 2017/0249033 A1 | 8/2017 | Podhajny et al. |
| 2017/0322633 A1 | 11/2017 | Shen et al. |
| 2017/0325337 A1 | 11/2017 | Karagozler et al. |
| 2017/0325518 A1 | 11/2017 | Poupyrev et al. |
| 2017/0329412 A1 | 11/2017 | Schwesig et al. |
| 2017/0329425 A1 | 11/2017 | Karagozler et al. |
| 2018/0000354 A1 | 1/2018 | DeBusschere et al. |
| 2018/0000355 A1 | 1/2018 | DeBusschere et al. |
| 2018/0004301 A1 | 1/2018 | Poupyrev |
| 2018/0046258 A1 | 2/2018 | Poupyrev |
| 2018/0177464 A1 | 6/2018 | Debusschere et al. |
| 2018/0296163 A1 | 10/2018 | Debusschere et al. |
| 2019/0391667 A1 | 12/2019 | Poupyrev |
| 2020/0218361 A1 | 7/2020 | Poupyrev |
| 2021/0132702 A1 | 5/2021 | Poupyrev |

FOREIGN PATENT DOCUMENTS

| | | |
|---|---|---|
| DE | 102013201359 | 7/2014 |
| EP | 0161895 | 11/1985 |
| EP | 1815788 | 8/2007 |
| EP | 2177017 | 4/2010 |
| EP | 2417908 | 2/2012 |
| EP | 2770408 | 8/2014 |
| EP | 2953007 | 12/2015 |
| EP | 3201726 | 8/2017 |
| GB | 2070469 | 9/1981 |
| GB | 2443208 | 4/2008 |
| JP | 2006234716 | 9/2006 |
| JP | 2007266772 | 10/2007 |
| JP | 2008287714 | 11/2008 |
| JP | 2008293501 | 12/2008 |
| JP | 2012198916 | 10/2012 |
| JP | 2012208714 | 10/2012 |
| JP | 2013251913 | 12/2013 |
| KR | 1020080102516 | 11/2008 |
| KR | 100987650 | 10/2010 |
| KR | 20130045222 | 5/2013 |
| KR | 20140053988 | 5/2014 |
| KR | 1020140055985 | 5/2014 |
| WO | 9001895 | 3/1990 |
| WO | 0130123 | 4/2001 |
| WO | 2001027855 | 4/2001 |
| WO | 0175778 | 10/2001 |
| WO | 2002082999 | 10/2002 |
| WO | 2004004557 | 1/2004 |
| WO | 2007125298 | 11/2007 |
| WO | 2009032073 | 3/2009 |
| WO | 2009083467 | 7/2009 |
| WO | 2010032173 | 3/2010 |
| WO | 2012026013 | 3/2012 |
| WO | 2012152476 | 11/2012 |
| WO | 2013082806 | 6/2013 |
| WO | 2013084108 | 6/2013 |
| WO | 2013137412 | 9/2013 |
| WO | 2013154864 | 10/2013 |
| WO | 2013186696 | 12/2013 |
| WO | 2013191657 | 12/2013 |
| WO | 2013192166 | 12/2013 |
| WO | 2014019085 | 2/2014 |
| WO | 2014085369 | 6/2014 |
| WO | 2014116968 | 7/2014 |
| WO | 2014124520 | 8/2014 |
| WO | 2014136027 | 9/2014 |
| WO | 2014138280 | 9/2014 |
| WO | 2014160893 | 10/2014 |
| WO | 2014165476 | 10/2014 |
| WO | 2014204323 | 12/2014 |
| WO | 2015017931 | 2/2015 |
| WO | 2015018675 | 2/2015 |
| WO | 2015022671 | 2/2015 |
| WO | WO-2015099796 A1 * | 7/2015 ........... A61B 5/0022 |
| WO | 2016053624 | 4/2016 |
| WO | 2016118534 | 7/2016 |
| WO | 2016176471 | 11/2016 |
| WO | 2016178797 | 11/2016 |
| WO | 2017019299 | 2/2017 |
| WO | 2017200571 | 11/2017 |
| WO | 20170200949 | 11/2017 |

OTHER PUBLICATIONS

Badawy, W. "System-on-Chip for Real-Time Applications" Springer Science & Business Media, 2003. Section 1.1, p. 3-16 (Year: 2003).*

"Final Office Action", U.S. Appl. No. 15/462,957, filed Nov. 8, 2019, 10 Pages.

"Non-Final Office Action", U.S. Appl. No. 15/791,044, filed Sep. 30, 2019, 22 Pages.

"Notice of Allowance", U.S. Appl. No. 15/462,957, filed Jan. 23, 2020, 8 Pages.

"Notice of Allowance", U.S. Appl. No. 15/791,044, filed Feb. 12, 2020, 8 Pages.

"Final Office Action", U.S. Appl. No. 14/504,121, dated Jul. 9, 2018, 23 pages.

"First Action Interview Office Action", U.S. Appl. No. 14/731,195, dated Jun. 21, 2018, 4 pages.

"Non-Final Office Action", U.S. Appl. No. 14/720,632, dated May 18, 2018, 20 pages.

"Non-Final Office Action", U.S. Appl. No. 14/809,901, dated May 24, 2018, 13 pages.

"Notice of Allowance", U.S. Appl. No. 14/715,793, dated Jul. 6, 2018, 5 pages.

"Non-Final Office Action", U.S. Appl. No. 15/462,957, dated May 24, 2019, 14 pages.

"Notice of Allowance", U.S. Appl. No. 15/703,511, dated Apr. 16, 2019, 5 pages.

"Notice of Allowance", U.S. Appl. No. 14/731,195, dated Apr. 24, 2019, 7 pages.

"European Search Report", European Application No. 16789735.4, dated Nov. 14, 2018, 4 pages.

"First Action Interview Office Action", U.S. Appl. No. 15/142,471, dated Feb. 5, 2019, 29 pages.

"First Examination Report", GB Application No. 1621332.4, dated May 16, 2017, 7 pages.

"Foreign Office Action", Japanese Application No. 2018156138, dated May 22, 2019, 3 pages.

"Foreign Office Action", British Application No. 1621192.2, dated Jun. 17, 2020, 5 pages.

"Foreign Office Action", Korean Application No. 1020197004803, dated Oct. 14, 2019, 2 pages.

"Foreign Office Action", CN Application No. 201680020123.9, dated Nov. 29, 2019, 10 pages.

"Foreign Office Action", European Application No. 16789735.4, dated Dec. 12, 2018, 5 pages.

"Foreign Office Action", Korean Application No. 1020197004803, dated Dec. 6, 2019, 2 pages.

"Foreign Office Action", Japanese Application No. 2018156138, dated Apr. 22, 2020, 3 pages.

"Foreign Office Action", Korean Application No. 1020197004803, dated Apr. 26, 2019, 6 pages.

"Foreign Office Action", Japanese Application No. 2018156138, dated Sep. 30, 2019, 3 pages.

"International Search Report and Written Opinion", PCT Application No. PCT/US2016/065295, dated Mar. 14, 2017, 12 pages.

(56) References Cited

OTHER PUBLICATIONS

"Non-Final Office Action", U.S. Appl. No. 15/704,825, dated Jun. 1, 2020, 22 Pages.
"Non-Final Office Action", U.S. Appl. No. 15/704,615, dated Jun. 1, 2020, 29 Pages.
"Non-Final Office Action", U.S. Appl. No. 15/596,702, dated Jan. 4, 2019, 10 pages.
"Pre-Interview Communication", U.S. Appl. No. 15/142,471, dated Dec. 12, 2018, 3 pages.
"Preliminary Report on Patentability", PCT Application No. PCT/US2016/065295, dated Jul. 24, 2018, 18 pages.
"Written Opinion", PCT Application No. PCT/US2016/065295, dated Apr. 13, 2018, 8 pages.
Antonimuthu, "Google's Project Soli brings Gesture Control to Wearables using Radar", YouTube[online], Available from https://www.youtube.com/watch?v=czJfcgvQcNA as accessed on May 9, 2017; See whole video, especially 6:05-6:35.
Duncan, "Motion Compensation of Synthetic Aperture Radar", Microwave Earth Remote Sensing Laboratory, Brigham Young University, Apr. 15, 2003, 5 pages.
"Final Office Action", U.S. Appl. No. 14/731,195, dated Oct. 11, 2018, 12 pages.
"Cardiio", Retrieved From: <http://www.cardiio.com/> Apr. 15, 2015 App Information Retrieved From: <https://itunes.apple.com/us/app/cardiio-touchless-camera-pulse/id542891434?ls=1&mt=8> Apr. 15, 2015, Feb. 24, 2015, 6 pages.
"Clever Toilet Checks on Your Health", CNN.Com; Technology, Jun. 28, 2005, 2 pages.
"Corrected Notice of Allowance", U.S. Appl. No. 14/582,896, dated Dec. 19, 2016, 2 pages
"Corrected Notice of Allowance", U.S. Appl. No. 14/504,061, dated Dec. 27, 2016, 2 pages.
"Corrected Notice of Allowance", U.S. Appl. No. 14/582,896, dated Feb. 6, 2017, 2 pages.
"Corrected Notice of Allowance", U.S. Appl. No. 14/582,896, dated Feb. 23, 2017, 2 pages.
"Corrected Notice of Allowance", U.S. Appl. No. 14/930,220, dated Mar. 20, 2017, 2 pages.
"Corrected Notice of Allowance", U.S. Appl. No. 14/930,220, dated May 11, 2017, 2 pages.
"Corrected Notice of Allowance", U.S. Appl. No. 14/312,486, dated Oct. 28, 2016, 4 pages.
"Corrected Notice of Allowance", U.S. Appl. No. 14/312,486, dated Jan. 23, 2017, 4 pages.
"Final Office Action", U.S. Appl. No. 14/504,061, dated Mar. 9, 2016, 10 pages.
"Final Office Action", U.S. Appl. No. 14/681,625, dated Dec. 7, 2016, 10 pages.
"Final Office Action", U.S. Appl. No. 15/398,147, dated Jun. 30, 2017, 11 pages.
"Final Office Action", U.S. Appl. No. 14/959,799, dated Jul. 19, 2017, 12 pages.
"Final Office Action", U.S. Appl. No. 14/715,454, dated Sep. 7, 2017, 14 pages.
"Final Office Action", U.S. Appl. No. 15/142,619, dated Feb. 8, 2018, 15 pages.
"Final Office Action", U.S. Appl. No. 14/504,121, dated Aug. 8, 2017, 16 pages.
"Final Office Action", U.S. Appl. No. 14/959,730, dated Nov. 22, 2017, 16 pages.
"Final Office Action", U.S. Appl. No. 14/959,799, dated Jan. 4, 2018, 17 pages.
"Final Office Action", U.S. Appl. No. 14/720,632, dated Jan. 9, 2018, 18 pages.
"Final Office Action", U.S. Appl. No. 14/518,863, dated May 5, 2017, 18 pages.
"Final Office Action", U.S. Appl. No. 14/959,901, dated Aug. 25, 2017, 19 pages.
"Final Office Action", U.S. Appl. No. 15/093,533, dated Mar. 21, 2018, 19 pages.
"Final Office Action", U.S. Appl. No. 14/715,454, dated Apr. 17, 2018, 19 pages.
"Final Office Action", U.S. Appl. No. 14/518,863, dated Apr. 5, 2018, 21 pages.
"Final Office Action", U.S. Appl. No. 14/599,954, dated Aug. 10, 2016, 23 pages.
"Final Office Action", U.S. Appl. No. 14/504,038, dated Sep. 27, 2016, 23 pages.
"Final Office Action", U.S. Appl. No. 15/403,066, dated Oct. 5, 2017, 31 pages.
"Final Office Action", U.S. Appl. No. 14/312,486, dated Jun. 3, 2016, 32 pages.
"Final Office Action", U.S. Appl. No. 14/699,181, dated May 4, 2018, 41 pages.
"Final Office Action", U.S. Appl. No. 14/715,793, dated Sep. 12, 2017, 7 pages.
"Final Office Action", U.S. Appl. No. 14/874,955, dated Jun. 30, 2017, 9 pages.
"First Action Interview OA", U.S. Appl. No. 14/715,793, dated Jun. 21, 2017, 3 pages.
"International Preliminary Report on Patentability", Application No. PCT/US2015/030388, dated Dec. 15, 2016, 12 pages.
"International Preliminary Report on Patentability", Application No. PCT/US2015/043963, dated Feb. 16, 2017, 12 pages.
"International Preliminary Report on Patentability", Application No. PCT/US2015/050903, dated Apr. 13, 2017, 12 pages.
"International Preliminary Report on Patentability", Application No. PCT/US2015/043949, dated Feb. 16, 2017, 13 pages.
"International Preliminary Report on Patentability", PCT Application No. PCT/US2016/026756, dated Oct. 19, 2017, 8 pages.
"International Preliminary Report on Patentability", Application No. PCT/US2015/044774, dated Mar. 2, 2017, 8 pages.
"International Search Report and Written Opinion", Application No. PCT/US2016/060399, dated Jan. 30, 2017, 11 pages.
"International Search Report and Written Opinion", Application No. PCT/US2015/044774, dated Nov. 3, 2015, 12 pages.
"International Search Report and Written Opinion", Application No. PCT/US2016/042013, dated Oct. 26, 2016, 12 pages.
"International Search Report and Written Opinion", Application No. PCT/US2016/062082, dated Feb. 23, 2017, 12 pages.
"International Search Report and Written Opinion", PCT/US2017/047691, dated Nov. 16, 2017, 13 pages.
"International Search Report and Written Opinion", Application No. PCT/US2016/024267, dated Jun. 20, 2016, 13 pages.
"International Search Report and Written Opinion", Application No. PCT/US2016/024273, dated Jun. 20, 2016, 13 pages.
"International Search Report and Written Opinion", Application No. PCT/US2016/032307, dated Aug. 25, 2016, 13 pages.
"International Search Report and Written Opinion", Application No. PCT/US2016/034366, dated Nov. 17, 2016, 13 pages.
"International Search Report and Written Opinion", Application No. PCT/US2016/029820, dated Jul. 15, 2016, 14 pages.
"International Search Report and Written Opinion", Application No. PCT/US2016/055671, dated Dec. 1, 2016, 14 pages.
"International Search Report and Written Opinion", Application No. PCT/US2016/030177, dated Aug. 2, 2016, 15 pages.
"International Search Report and Written Opinion", PCT Application No. PCT/US2017/051663, dated Nov. 29, 2017, 16 pages.
"International Search Report and Written Opinion", Application No. PCT/US2015/043963, dated Nov. 24, 2015, 16 pages.
"International Search Report and Written Opinion", Application No. PCT/US2016/024289, dated Aug. 25, 2016, 17 pages.
"International Search Report and Written Opinion", Application No. PCT/US2015/043949, dated Dec. 1, 2015, 18 pages.
"International Search Report and Written Opinion", Application No. PCT/US2015/050903, dated Feb. 19, 2016, 18 pages.
"International Search Report and Written Opinion", Application No. PCT/US2016/030115, dated Aug. 8, 2016, 18 pages.
"International Search Report and Written Opinion", Application No. PCT/US2016/063874, dated May 11, 2017, 19 pages.
"International Search Report and Written Opinion", Application No. PCT/US2016/033342, dated Oct. 27, 2016, 20 pages.

(56) References Cited

OTHER PUBLICATIONS

"Life:X Lifestyle explorer", Retrieved from <https://web.archive.org/web/20150318093841/http://research.microsoft.com/en-us/projects/lifex >, Feb. 3, 2017, 2 pages.
"Non-Final Office Action", U.S. Appl. No. 14/504,139, dated Jan. 27, 2017, 10 pages.
"Non-Final Office Action", U.S. Appl. No. 14/959,799, dated Jan. 27, 2017, 10 pages.
"Non-Final Office Action", U.S. Appl. No. 15/398,147, dated Mar. 9, 2017, 10 pages.
"Non-Final Office Action", U.S. Appl. No. 14/504,139, dated Oct. 18, 2017, 12 pages.
"Non-Final Office Action", U.S. Appl. No. 14/666,155, dated Feb. 3, 2017, 12 pages.
"Non-Final Office Action", U.S. Appl. No. 14/504,121, dated Jan. 9, 2017, 13 pages.
"Non-Final Office Action", U.S. Appl. No. 14/959,730, dated Jun. 23, 2017, 14 pages.
"Non-Final Office Action", U.S. Appl. No. 14/862,409, dated Jun. 22, 2017, 15 pages.
"Non-Final Office Action", U.S. Appl. No. 14/930,220, dated Sep. 14, 2016, 15 pages.
"Non-Final Office Action", U.S. Appl. No. 14/720,632, dated Jun. 14, 2017, 16 pages.
"Non-Final Office Action", U.S. Appl. No. 15/142,619, dated Aug. 25, 2017, 16 pages.
"Non-Final Office Action", U.S. Appl. No. 14/959,799, dated Sep. 8, 2017, 16 pages.
"Non-Final Office Action", U.S. Appl. No. 14/715,454, dated Jan. 11, 2018, 16 pages.
"Non-Final Office Action", U.S. Appl. No. 15/595,649, dated Oct. 31, 2017, 16 pages.
"Non-Final Office Action", U.S. Appl. No. 14/518,863, dated Oct. 14, 2016, 16 pages.
"Non-Final Office Action", U.S. Appl. No. 14/599,954, dated Jan. 26, 2017, 16 pages.
"Non-Final Office Action", U.S. Appl. No. 14/862,409, dated Dec. 14, 2017, 17 pages.
"Non-Final Office Action", U.S. Appl. No. 14/599,954, dated Feb. 2, 2016, 17 pages.
"Non-Final Office Action", U.S. Appl. No. 15/093,533, dated Aug. 24, 2017, 18 pages.
"Non-Final Office Action", U.S. Appl. No. 15/142,689, dated Oct. 4, 2017, 18 pages.
"Non-Final Office Action", U.S. Appl. No. 14/504,121, dated Jan. 2, 2018, 19 pages.
"Non-Final Office Action", U.S. Appl. No. 14/518,863, dated Sep. 29, 2017, 20 pages.
"Non-Final Office Action", U.S. Appl. No. 14/959,901, dated Jan. 8, 2018, 21 pages.
"Non-Final Office Action", U.S. Appl. No. 14/504,038, dated Feb. 26, 2016, 22 pages.
"Non-Final Office Action", U.S. Appl. No. 14/312,486, dated Oct. 23, 2015, 25 pages.
"Non-Final Office Action", U.S. Appl. No. 15/267,181, dated Feb. 8, 2018, 29 pages.
"Non-Final Office Action", U.S. Appl. No. 15/403,066, dated May 4, 2017, 31 pages.
"Non-Final Office Action", U.S. Appl. No. 14/699,181, dated Oct. 18, 2017, 33 pages.
"Non-Final Office Action", U.S. Appl. No. 14/504,038, dated Mar. 22, 2017, 33 pages.
"Non-Final Office Action", U.S. Appl. No. 15/398,147, dated Sep. 8, 2017, 7 pages.
"Non-Final Office Action", U.S. Appl. No. 14/874,955, dated Feb. 8, 2018, 7 pages.
"Non-Final Office Action", U.S. Appl. No. 14/681,625, dated Mar. 6, 2017, 7 pages.
"Non-Final Office Action", U.S. Appl. No. 14/504,061, dated Nov. 4, 2015, 8 pages.
"Non-Final Office Action", U.S. Appl. No. 14/874,955, dated Feb. 27, 2017, 8 pages.
"Non-Final Office Action", U.S. Appl. No. 14/582,896, dated Jun. 29, 2016, 9 pages.
"Non-Final Office Action", U.S. Appl. No. 14/681,625, dated Aug. 12, 2016, 9 pages.
"Non-Final Office Action", U.S. Appl. No. 14/666,155, dated Aug. 24, 2016, 9 pages.
"Non-Final Office Action", U.S. Appl. No. 14/513,875, dated Feb. 21, 2017, 9 pages.
"Notice of Allowance", U.S. Appl. No. 14/599,954, dated May 24, 2017, 11 pages.
"Notice of Allowance", U.S. Appl. No. 14/312,486, dated Oct. 7, 2016, 15 pages.
"Notice of Allowance", U.S. Appl. No. 14/504,038, dated Aug. 7, 2017, 17 pages.
"Notice of Allowance", U.S. Appl. No. 15/403,066, dated Jan. 8, 2018, 18 pages.
"Notice of Allowance", U.S. Appl. No. 14/715,793, dated Dec. 18, 2017, 5 pages.
"Notice of Allowance", U.S. Appl. No. 14/666,155, dated Feb. 20, 2018, 5 pages.
"Notice of Allowance", U.S. Appl. No. 14/582,896, dated Nov. 7, 2016, 5 pages.
"Notice of Allowance", U.S. Appl. No. 14/513,875, dated Jun. 28, 2017, 7 pages.
"Notice of Allowance", U.S. Appl. No. 14/666,155, dated Jul. 10, 2017, 7 pages.
"Notice of Allowance", U.S. Appl. No. 14/874,955, dated Oct. 20, 2017, 7 pages.
"Notice of Allowance", U.S. Appl. No. 14/504,061, dated Sep. 12, 2016, 7 pages.
"Notice of Allowance", U.S. Appl. No. 14/494,863, dated May 30, 2017, 7 pages.
"Notice of Allowance", U.S. Appl. No. 14/681,625, dated Jun. 7, 2017, 7 pages.
"Notice of Allowance", U.S. Appl. No. 14/681,625, dated Oct. 23, 2017, 8 pages.
"Notice of Allowance", U.S. Appl. No. 15/398,147, dated Nov. 15, 2017, 8 pages.
"Notice of Allowance", U.S. Appl. No. 14/959,730, dated Feb. 22, 2018, 8 pages.
"Notice of Allowance", U.S. Appl. No. 14/930,220, dated Feb. 2, 2017, 8 pages.
"Notice of Allowance", U.S. Appl. No. 15/343,067, dated Jul. 27, 2017, 9 pages.
"Notice of Allowance", U.S. Appl. No. 14/599,954, dated Mar. 15, 2018, 9 pages.
"Philips Vital Signs Camera", Retrieved From: <http://www.vitalsignscamera.com/> Apr. 15, 2015, Jul. 17, 2013, 2 pages.
"Pre-Interview Communication", U.S. Appl. No. 14/513,875, dated Oct. 21, 2016, 3 pages.
"Pre-Interview Communication", U.S. Appl. No. 14/715,793, dated Mar. 20, 2017, 3 pages.
"Pre-Interview Communication", U.S. Appl. No. 14/715,454, dated Apr. 14, 2017, 3 pages.
"Pre-Interview Communication", U.S. Appl. No. 14/494,863, dated Jan. 27, 2017, 5 pages.
"Pre-Interview Office Action", U.S. Appl. No. 14/731,195, dated Dec. 20, 2017, 4 pages.
"Preliminary Report on Patentability", PCT Application No. PCT/US2016/042013, dated Jan. 30, 2018, 7 pages.
"Preliminary Report on Patentability", PCT Application No. PCT/US2016/032307, dated Dec. 7, 2017, 9 pages.
"The Dash smart earbuds play back music, and monitor your workout", Retrieved from < http://newatlas.com/bragi-dash-tracking-earbuds/30808/>, Feb. 13, 2014, 3 pages.
"The Instant Blood Pressure app estimates blood pressure with your smartphone and our algorithm", Retrieved at http://www.instantbloodpressure.com/—on Jun. 23, 2016, 6 pages.
"Thermofocus No Touch Forehead Thermometer", Technimed, Internet Archive. Dec. 24, 2014. https://web.archive.org/web/

(56) References Cited

OTHER PUBLICATIONS

20141224070848/http://www.tecnimed.it:80/thermofocus-forehead-thermometer-H1N1-swine-flu.html, Dec. 24, 2018, 4 pages.

Balakrishnan, Guha et al., "Detecting Pulse from Head Motions in Video", In Proceedings: CVPR '13 Proceedings of the 2013 IEEE Conference on Computer Vision and Pattern Recognition Available at: <http://people.csail.mit.edu/mrub/vidmag/papers/Balakrishnan_Detecting_Pulse_from_2013_CVPR_paper.pdf>, Jun. 23, 2013, 8 pages.

Couderc, Jean-Philippe et al., "Detection of Atrial Fibrillation using Contactless Facial Video Monitoring", In Proceedings: Heart Rhythm Society, vol. 12, Issue 1 Available at: <http://www.heartrhythmjournal.com/article/S1547-5271(14)00924-2/pdf>, 7 pages.

Espina, Javier et al., "Wireless Body Sensor Network for Continuous Cuff-less Blood Pressure Monitoring", International Summer School on Medical Devices and Biosensors, 2006, 5 pages.

He, David D. "A Continuous, Wearable, and Wireless Heart Monitor Using Head Ballistocardiogram (BCG) and Head Electrocardiogram (ECG) with a Nanowatt ECG Heartbeat Detection Circuit", In Proceedings: Thesis, Department of Electrical Engineering and Computer Science, Massachusetts Institute of Technology Available at: <http://dspace.mit.edu/handle/1721.1/79221>, 137 pages.

Klabunde, Richard E. "Ventricular Pressure-Volume Loop Changes in Valve Disease", Retrieved From <https://web.archive.org/web/20101201185256/http://cvphysiology.com/Heart%20Disease/HD009.htm>, Dec. 1, 2010, 8 pages.

Matthews, Robert J. "Venous Pulse", Retrieved at: http://www.rjmatthewsmd.com/Definitions/venous_pulse.htm—on Nov. 30, 2016, Apr. 13, 2013, 7 pages.

Nakajima, Kazuki et al., "Development of Real-Time Image Sequence Analysis for Evaluating Posture Change and Respiratory Rate of a Subject in Bed", In Proceedings: Physiological Measurement, vol. 22, No. 3 Retrieved From: <http://iopscience.iop.org/0967-3334/22/3/401/pdf/0967-3334_22_3_401.pdf> Feb. 27, 2015, 8 pages.

Otto, Chris et al., "System Architecture of a Wireless Body Area Sensor Network for Ubiquitous Health Monitoring", Journal of Mobile Multimedia; vol. 1, No. 4, Jan. 10, 2006, 20 pages.

Palese, et al., "The Effects of Earphones and Music on the Temperature Measured by Infrared Tympanic Thermometer: Preliminary Results", ORL—head and neck nursing: official journal of the Society of Otorhinolaryngology and Head-Neck Nurses 32.2, Jan. 1, 2013, pp. 8-12.

Poh, Ming-Zher et al., "A Medical Mirror for Non-contact Health Monitoring", In Proceedings: ACM SIGGRAPH Emerging Technologies Available at: <http://affect.media.mit.edu/pdfs/11.Poh-etal-SIGGRAPH.pdf>, Jan. 1, 2011, 1 page.

Poh, Ming-Zher et al., "Non-contact, Automated Cardiac Pulse Measurements Using Video Imaging and Blind Source Separation.", In Proceedings: Optics Express, vol. 18, No. 10 Available at: <http://www.opticsinfobase.org/view_article.cfm?gotourl=http%3A%2F%2Fwww%2Eopticsinfobase%2Eorg%2FDirectPDFAccess%2F77B04D55%2DBC95%2D6937%2D5BAC49A426378C02%5F199381%2Foe%2D18%2D10%2D10762%2Ep, May 7, 2010, 13 pages.

Wang, Wenjin et al., "Exploiting Spatial Redundancy of Image Sensor for Motion Robust rPPG", In Proceedings: IEEE Transactions on Biomedical Engineering, vol. 62, Issue 2, Jan. 19, 2015, 11 pages.

"Final Office Action", U.S. Appl. No. 14/809,901, dated Dec. 13, 2018, 7 pages.

"Pre-Interview Communication", U.S. Appl. No. 15/703,511, dated Feb. 11, 2019, 5 pages.

"Restriction Requirement", U.S. Appl. No. 15/462,957, dated Jan. 4, 2019, 6 pages.

"Advisory Action", U.S. Appl. No. 14/504,139, dated Aug. 28, 2017, 3 pages.

"Advisory Action", U.S. Appl. No. 15/704,825, filed Feb. 10, 2021, 4 pages.

"Apple Watch Used Four Sensors to Detect your Pulse", retrieved from http://www.theverge.com/2014/9/9/6126991 / apple-watch-four-back-sensors-detect-activity on Sep. 23, 2017 as cited in PCT search report for PCT Application No. PCT/US2016/026756 on Nov. 10, 2017; The Verge, paragraph 1, Sep. 9, 2014, 4 pages.

"Combined Search and Examination Report", GB Application No. 1620892.8, dated Apr. 6, 2017, 5 pages.

"Combined Search and Examination Report", GB Application No. 1620891.0, dated May 31, 2017, 9 pages.

"Corrected Notice of Allowance", U.S. Appl. No. 16/560,085, filed Jan. 28, 2021, 2 pages.

"Corrected Notice of Allowance", U.S. Appl. No. 16/560,085, filed Dec. 14, 2020, 2 pages.

"Extended European Search Report", EP Application No. 15170577.9, dated Nov. 5, 2015, 12 pages.

"Extended European Search Report", EP Application No. 20174555.1, dated Oct. 13, 2020, 9 pages.

"Final Office Action", U.S. Appl. No. 15/704,825, filed Nov. 23, 2020, 18 pages.

"Final Office Action", U.S. Appl. No. 15/704,615, filed Dec. 11, 2020, 26 pages.

"First Action Interview Office Action", U.S. Appl. No. 14/959,901, dated Apr. 14, 2017, 3 pages.

"First Action Interview Office Action", U.S. Appl. No. 15/286,152, dated Mar. 1, 2018, 5 pages.

"First Action Interview Pilot Program Pre-Interview Communication", U.S. Appl. No. 14/731,195, dated Aug. 1, 2017, 3 pages.

"Foreign Office Action", KR Application No. 10-2016-7036023, dated Aug. 11, 2017, 10 pages.

"Foreign Office Action", GB Application No. 1621191.4, dated Dec. 31, 2020, 4 pages.

"Foreign Office Action", CN Application No. 201721290290.3, dated Mar. 9, 2018, 4 pages.

"Foreign Office Action", KR Application No. 10-2016-7035397, dated Sep. 20, 2017, 5 pages.

"Foreign Office Action", KR Application No. 10-2019-7004803, dated Jan. 21, 2021, 6 pages.

"Foreign Office Action", EP Application No. 15170577.9, dated May 30, 2017, 7 pages.

"Foreign Office Action", JP Application No. 2016-567813, dated Sep. 22, 2017, 8 pages.

"Foreign Office Action", EP Application No. 15754323.2, dated Mar. 9, 2018, 8 pages.

"Frogpad Introduces Wearable Fabric Keyboard with Bluetooth Technology", Retrieved From: <http://www.geekzone.co.nz/content.asp?contentid=3898> Mar. 16, 2015, Jan. 7, 2005, 2 pages.

"Non-Invasive Quantification of Peripheral Arterial Volume Distensibilitiy and its Non-Lineaer Relationship with Arterial Pressure", Journal of Biomechanics, Pergamon Press, vol. 42, No. 8; as cited in the search report for PCT/US2016/013968 citing the whole document, but in particular the abstract, May 29, 2009, 2 pages.

"Notice of Allowability", U.S. Appl. No. 16/560,085, filed Nov. 12, 2020, 2 pages.

"Notice of Allowance", U.S. Appl. No. 16/560,085, filed Oct. 19, 2020, 8 pages.

"Pre-Interview Communication", U.S. Appl. No. 14/959,901, dated Feb. 10, 2017, 4 pages.

"Pre-Interview Communication", U.S. Appl. No. 14/959,730, dated Feb. 15, 2017, 4 pages.

"Pre-Interview Communication", U.S. Appl. No. 15/166,198, dated Mar. 8, 2018, 8 pages.

"Pre-Interview First Office Action", U.S. Appl. No. 15/286,152, dated Feb. 8, 2018, 4 pages.

"Pre-Interview Office Action", U.S. Appl. No. 14/862,409, dated Sep. 15, 2017, 16 pages.

"Pressure-Volume Loop Analysis in Cardiology", retrieved from https://en.wikipedia.org/w/index.php?title=Pressure-volume loop analysis in card iology&oldid=636928657 on Sep. 23, 2017; Obtained per link provided in search report from PCT/US2016/01398 on Jul. 28, 2016, Dec. 6, 2014, 10 pages.

"Restriction Requirement", U.S. Appl. No. 15/362,359, dated Jan. 8, 2018, 5 pages.

"Restriction Requirement", U.S. Appl. No. 14/666,155, dated Jul. 22, 2016, 5 pages.

(56) References Cited

OTHER PUBLICATIONS

"Textile Wire Brochure", Retrieved at: http://www.textile-wire.ch/en/home.html, Aug. 7, 2004, 17 pages.
"Written Opinion", Application No. PCT/US2017/032733, dated Jul. 26, 2017, 5 pages.
"Written Opinion", Application No. PCT/US2016/042013, dated Feb. 2, 2017, 6 pages.
"Written Opinion", Application No. PCT/US2016/026756, dated Nov. 10, 2016, 7 pages.
"Written Opinion", Application No. PCT/US2016/013968, dated Jul. 28, 2016, 9 pages.
Arbabian, Amin et al., "A 94GHz mm-Wave to Baseband Pulsed-Radar for Imaging and Gesture Recognition", 2012 IEEE, 2012 Symposium on VLSI Circuits Digest of Technical Papers, Jan. 1, 2012, 2 pages.
Bondade, Rajdeep et al., "A linear-assisted DC-DC hybrid power converter for envelope tracking RF power amplifiers", 2014 IEEE Energy Conversion Congress and Exposition (ECCE), IEEE, Sep. 14, 2014, pp. 5769-5773, XP032680873, DOI: 10.1109/ECCE.2014.6954193, Sep. 14, 2014, 5 pages.
Cheng, Jingyuan "Smart Textiles: From Niche to Mainstream", IEEE Pervasive Computing, Jul. 2013, pp. 81-84.
Fan, Tenglong et al., "Wireless Hand Gesture Recognition Based on Continuous-Wave Doppler Radar Sensors", IEEE Transactions on Microwave Theory and Techniques, Plenum, USA, vol. 64, No. 11, Nov. 1, 2016 (Nov. 1, 2016), pp. 4012-4012, XP011633246, ISSN: 0018-9480, DOI: 10.1109/TMTT.2016.2610427, Nov. 1, 2016, 9 pages.
Farringdon, Jonny et al., "Wearable Sensor Badge & Sensor Jacket for Context Awareness", Third International Symposium on Wearable Computers, Sep. 2000, 7 pages.
Godana, Bruhtesfa E. "Human Movement Characterization in Indoor Environment using GNU Radio Based Radar", Nov. 30, 2009, 100 pages.
Holleis, Paul et al., "Evaluating Capacitive Touch Input on Clothes", Proceedings of the 10th International Conference on Human Computer Interaction, Jan. 1, 2008, 10 pages.
Ishijima, Masa "Unobtrusive Approaches to Monitoring Vital Signs at Home", Medical & Biological Engineering and Computing, Springer, Berlin, DE, vol. 45, No. 11 as cited in search report for PCT/US2016/013968 on Jul. 28, 2016, Sep. 26, 2007, 3 pages.
Lien, Jaime et al., "Soli: Ubiquitous Gesture Sensing with Millimeter Wave Radar", ACM Transactions on Graphics (TOG), ACM, Us, vol. 35, No. 4, Jul. 11, 2016 (Jul. 11, 2016), pp. 1-19, XP058275791, ISSN: 0730-0301, DOI: 10.1145/2897824.2925953, Jul. 11, 2016, 19 pages.
Martinez-Garcia, Hermino et al., "Four-quadrant linear-assisted DC/DC voltage regulator", Analog Integrated Circuits and Signal Processing, Springer New York LLC, US, vol. 88, No. 1, Apr. 23, 2016 (Apr. 23, 2016)pp. 151-160, XP035898949, ISSN: 0925-1030, DOI: 10.1007/S10470-016-0747-8, Apr. 23, 2016, 10 pages.
Patel, P C. et al., "Applications of Electrically Conductive Yarns in Technical Textiles", International Conference on Power System Technology (POWECON), Oct. 30, 2012, 6 pages.
Pu, Qifan et al., "Gesture Recognition Using Wireless Signals", Oct. 2014, pp. 15-18.
Pu, Qifan et al., "Whole-Home Gesture Recognition Using Wireless Signals", Proceedings of the 19th annual international conference on Mobile computing & networking (MobiCom'13), US, ACM, Sep. 30, 2013, pp. 27-38, Sep. 30, 2013, 12 pages.
Schneegass, Stefan et al., "Towards a Garment OS: Supporting Application Development for Smart Garments", Wearable Computers, ACM, Sep. 13, 2014, 6 pages.
Skolnik, Merrill I. "CW and Frequency-Modulated Radar", In: "Introduction to Radar Systems", Jan. 1, 1981 (Jan. 1, 1981), McGraw Hill, XP055047545, ISBN: 978-0-07-057909-5 pp. 68-100, p. 95-p. 97, Jan. 1, 1981, 18 pages.
Stoppa, Matteo "Wearable Electronics and Smart Textiles: A Critical Review", In Proceedings of Sensors, vol. 14, Issue 7, Jul. 7, 2014, pp. 11957-11992.
Wang, Yazhou et al., "Micro-Doppler Signatures for Intelligent Human Gait Recognition Using a UWB Impulse Radar", 2011 IEEE International Symposium on Antennas and Propagation (APSURSI), Jul. 3, 2011, pp. 2103-2106.
Wijesiriwardana, R et al., "Capacitive Fibre-Meshed Transducer for Touch & Proximity Sensing Applications", IEEE Sensors Journal, IEEE Service Center, Oct. 1, 2005, 5 pages.
Zhadobov, Maxim et al., "Millimeter-wave Interactions with the Human Body: State of Knowledge and Recent Advances", International Journal of Microwave and Wireless Technologies, Mar. 1, 2011, 11 pages.
Zhang, Ruquan et al., "Study of the Structural Design and Capacitance Characteristics of Fabric Sensor", Advanced Materials Research (vols. 194-196), Feb. 21, 2011, 8 pages.
Zheng, Chuan et al., "Doppler Bio-Signal Detection Based Time-Domain Hand Gesture Recognition", 2013 IEEE MTT-S International Microwave Workshop Series on RF and Wireless Technologies for Biomedical and Healthcare Applications (IMWS-BIO), IEEE, Dec. 9, 2013 (Dec. 9, 2013), p. 3, XP032574214, DOI: 10.1109/IMWS-BIO.2013.6756200, Dec. 9, 2013, 3 Pages.
"Non-Final Office Action", U.S. Appl. No. 16/822,601, filed Mar. 15, 2021, 17 pages.
"Notice of Allowance", U.S. Appl. No. 14/504,121, filed Jun. 1, 2021, 8 pages.
"Patent Board Decision", U.S. Appl. No. 14/504,121, May 20, 20201, 9 pages.
"Foreign Office Action", GB Application No. 1621191.4, dated Jun. 23, 2021, 4 pages.
"Foreign Office Action", GB Application No. 1621191.4, dated Sep. 10, 2021, 3 pages.
"Notice of Allowance", U.S. Appl. No. 16/822,601, filed Aug. 5, 2021, 9 pages.
"Foreign Office Action", EP Application No. 16789735.4, dated Oct. 5, 2021, 5 pages.
"Notice of Allowance", U.S. Appl. No. 17/148,374, filed Oct. 14, 2021, 8 pages.

* cited by examiner

IN-EAR HEALTH MONITORING

PRIORITY

This application is a continuation of and claims priority to U.S. patent application Ser. No. 14/666,155 filed Mar. 23, 2015 entitled "In-Ear Health Monitoring", the disclosure of which is incorporated by reference herein in its entirety.

BACKGROUND

Currently, when a person is potentially exposed to a contagious disease, such as Ebola, the person can be put into quarantine, asked to regularly come in to a hospital or doctor's office, or asked to track their own health. Each of these methods, however, has significant drawbacks. Placing a person in quarantine is expensive, can be illegal absent some imminent threat, and removes the quarantined persons from his or her productive pursuits. Asking a person to regularly visit a facility to check their health has highly irregular results and, due to the artificial atmosphere in which health monitoring is performed, is often not reliable at catching an infection early. Asking a person to track their own health also has many drawbacks, including compliance, poor data, and failure to detect the infection before others are infected and often after the best outcome for that person can be attained through early detection.

SUMMARY

This document describes techniques for, and systems that enable, in-ear health monitoring. The techniques described enable early detection of contagious disease through use of an in-ear health-monitoring and audio device. These techniques prompt a user, often through the user's smart phone, to listen to audio content through the device, which also takes the user's temperature. Through repetitive use, the techniques are capable of determining a temperature differential for the user, which aids in early detection of a contagious disease or other potential health condition.

This document also describes a wired, in-ear health-monitoring and audio device that is capable of rendering audio content and measuring a person's temperature in conjunction with the person's mobile computing device through an audio socket of that device. This wired, in-ear device can, in some embodiments, be made cheaply and compatible with many common mobile computing devices, such as smart phones, tablets, smart watches, and audio players. In cases where a contagious disease breaks out, such as Ebola or the Swine Flu, these wired, in-ear devices can be given out to hundreds if not thousand or tens of thousands of people and, by so doing, enable early detection of the contagious disease. This early detection not only increases the chances that the infected person will survive, it can also substantially curb or reduce the spread of the contagious disease.

This summary is provided to introduce simplified concepts concerning in-ear health monitoring, which is further described below in the Detailed Description. This summary is not intended to identify essential features of the claimed subject matter, nor is it intended for use in determining the scope of the claimed subject matter.

BRIEF DESCRIPTION OF THE DRAWINGS

Embodiments of techniques and devices for in-ear health monitoring are described with reference to the following drawings. The same numbers are used throughout the drawings to reference like features and components.

DETAILED DESCRIPTION

Overview

Figure 1:
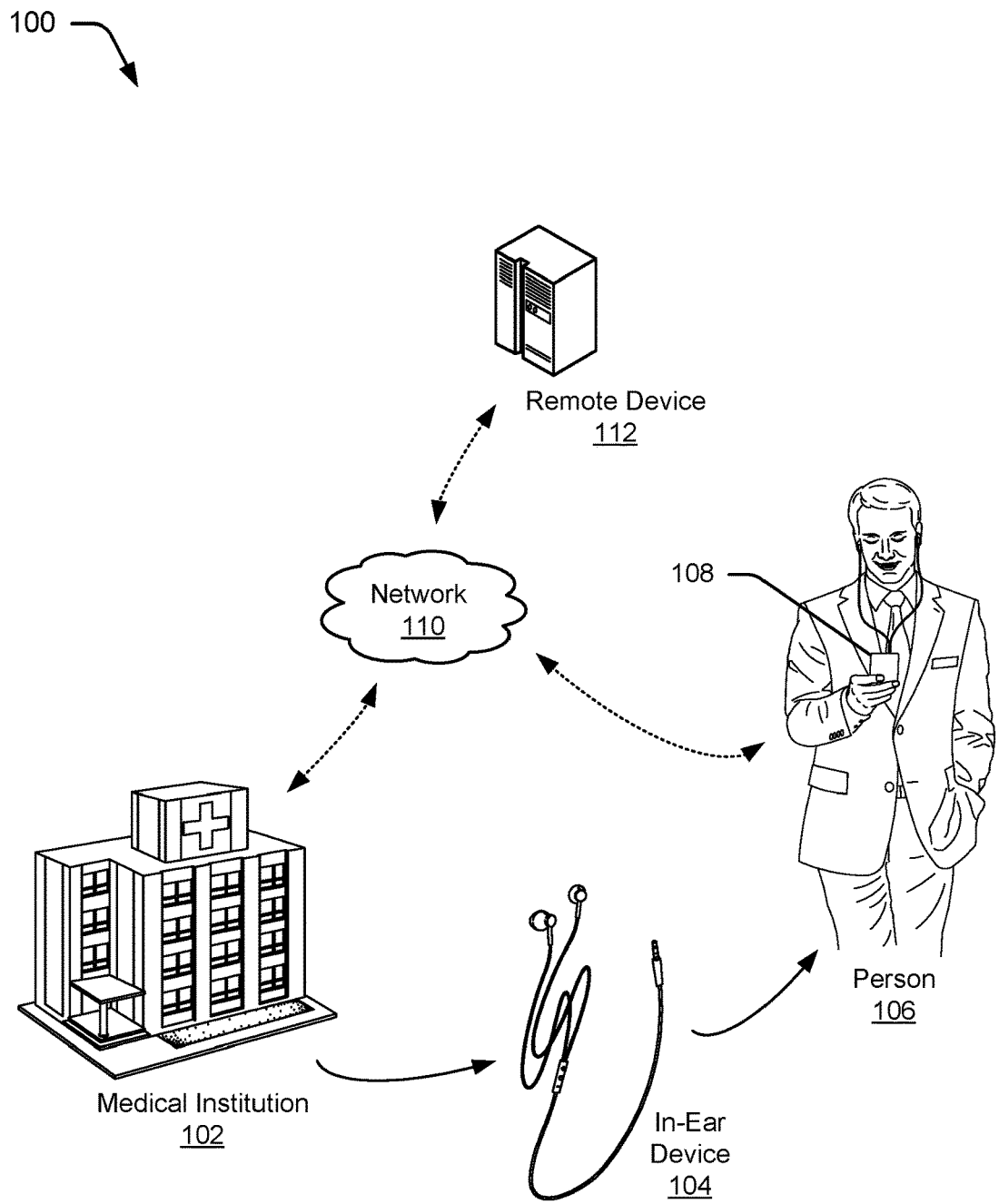
FIG. 1 illustrates an example environment in which in-ear health monitoring can be implemented.

This document describes techniques using, and devices enabling, in-ear health monitoring. Through use of these techniques and devices, early detection of contagious diseases can be made. This can decrease mortality for particular persons using the device as well as others around them by reducing the disease's spread.

Consider, for example, a situation where a person that has contracted the Ebola virus travels through an airport in Sierra Leone, gets on a first plane to London, spends three hours in London, and travels on a second plane to Tokyo, Japan, and then spends one hour in the Tokyo airport before taking a tram to a hotel outside of the city. The next day the person feels ill and takes a taxi to a local hospital. As can easily be seen from this example, every person on both planes, all three airports, the tram, the taxi driver, and the medical professions that take care of the person when he gets to the local airport, at least all of these people should be monitored for Ebola. This amounts to many hundreds of people. To be safer, those people in the airports, the security persons, those at nearby gates, and those in the hotel should also be monitored, increasing the numbers to thousands of people.

Current early-detection protocols are nearly useless to address this type of widespread exposure—quarantining all of these people is impractical, asking all of them to regularly visit their medical professionals is highly unlikely to catch the disease early due to inaccurate measurement, little or no temperature differential, or non-compliance and if all of them did comply, they would overwhelm the ability of their local medical offices to help them, as well as increase exposure to people in those offices. Asking each of them to monitor themselves could help somewhat, but by the time a person feels sick they are already contagious to others and detection is too late to substantially improve their chances of survival. Even in the unlikely event that most of these people monitor themselves through use of some traditional health monitors, such as in-mouth thermometers, the results are unreliable and sporadic, thereby failing to catch the disease early enough to be of most benefit to them and others.

Contrast these current early-detection protocols with the techniques and systems described herein. These techniques are cheap to implement, strongly encourage people to monitor themselves through reminders or compensation, and provide more-accurate detection. Contrasted with the above example, in-ear health-monitoring and audio devices can be handed out in the thousands—even at a cost of less than one U.S. dollar per device. They can be administered even without having to directly contact every person—they can simply be waiting at major health offices for use by persons that hear on the radio or television or the Internet that the person with Ebola was at an airport the same time as they remember being there. Further, as will be described in detail below, these in-ear devices are capable of early detection of small temperature changes in a person's core temperature. In some cases, changes that indicate a possible infection can be supplied to local health professionals and disease-control institutions or simply the person herself so that she can immediately follow on-screen instructions to get medical attention in a responsible way.

This is but one example of how the techniques and devices enable in-ear health monitoring. Other examples are described below. This document now turns to an example environment, after which example wired and wireless in-ear devices, methods, a user interface, and an example computing system are described.

Example Environment

FIG. 1 is an illustration of an example environment 100 in which in-ear health monitoring can be employed. Environment 100 illustrates a medical institution 102 providing an in-ear health-monitoring and audio device (in-ear device) 104 to a person 106. In-ear device 104 can be used in conjunction with a mobile computing device 108. Data, such as sensor data, temperature data, or a temperature differential can be provided by mobile computing device 108 through a communication network 110 to a remote device 112 and/or medical institution 102. As will be described later herein, in-ear device 104 can be used to monitor person 106's health in real life. The frequency and situations in which this monitoring are performed can vary based on the disease to which the person may have been exposed, which may alter the frequency and situations at which monitoring is prompted by a monitoring module operating through mobile computing device 108. Example frequencies are every four or eight hours, twice a day at same times or same situations (e.g., after eating, during exercise, when lying down for bed). Also, entities at remote device 112 and/or medical institution 102 may interact with person 106 or his or her mobile computing device 108 to better monitor person 106's health, as shown with communication through network 110.

Person 106 may receive in-ear device 104 directly from medical institution 102 or through another entity, such as brick-and-mortar pharmacy, government entity tasked with disease control, through the mail, and so forth. In-ear device 104 or a health managing module can customize the use of in-ear device 104 as noted above, though this is not strictly required.

Network 110 includes one or more of many types of wireless or partly wireless communication networks, such as a local-area-network (LAN), a wireless local-area-network (WLAN), a personal-area-network (PAN), a wide-area-network (WAN), near-field communication (NFC), an intranet, the Internet, a peer-to-peer network, point-to-point network, a mesh network, and so forth. As will be addressed below, in-ear device 104, in some cases, is a wireless rather than wired device. In such cases, network 110 can be used for communication between in-ear device 104 and mobile computing device 108 (or even non-mobile or remote devices, such as directly with remote device 112).

Figure 2:
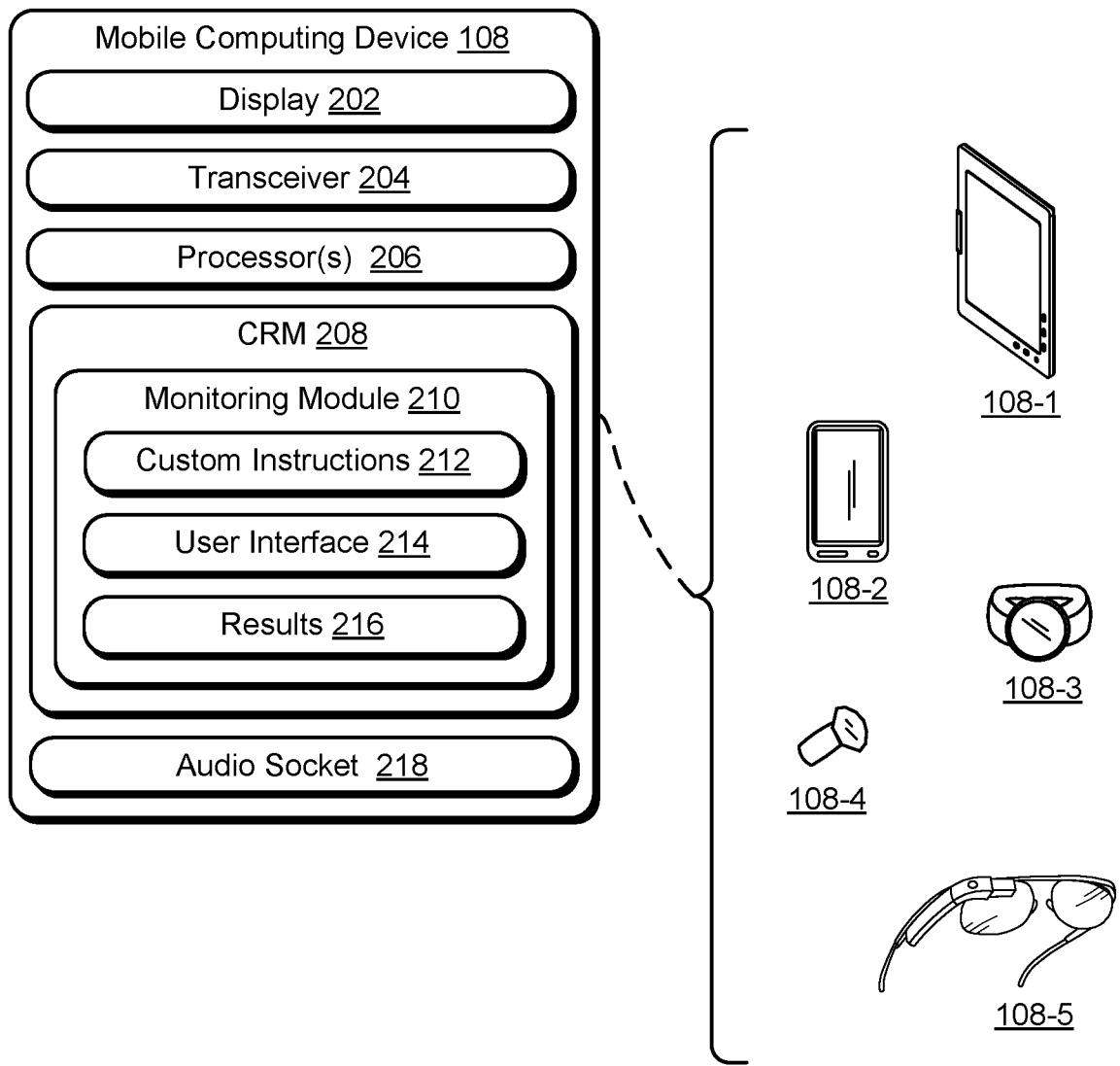
FIG. 2 illustrates an example mobile computing device of FIG. 1.

With regard to the example mobile computing device 108 of FIG. 1, consider a detailed illustration in FIG. 2. Mobile computing device 108 can be one or a combination of various devices, here illustrated with five examples: a tablet computer 108-1, a smartphone 108-2, a computing watch 108-3, a computing ring 108-4, and computing spectacles 108-5, though other computing devices and systems, such as a wearable computing device or laptop computer, may also be used. As will be noted in greater detail below, in some embodiments the techniques operate through remote device 112. In such cases, mobile computing device 108 may forgo performing some or all of the computing operations relating to the techniques, and thus need not be capable of advanced computing operations.

Mobile computing device 108 includes or is able to communicate with a display 202 (five are shown in FIG. 2), a transceiver 204, one or more processors 206, and computer-readable storage media 208 (CRM 208). CRM 208 includes monitoring module 210, which includes or has access to custom instructions 212, user interface 214, and results 216. Custom instructions 212 are not required, though use of custom instructions 212 may, in some cases, be useful for particular diseases or may improve robustness and accuracy of data from in-ear device 104.

More specifically, custom instructions 212 may require health-monitoring by in-ear device 104 to be made at particular times or situations, which can be real-life situations, such as the person eating, sleeping for a period of time, walking, running, or undergoing stress. Further, these real-life situations can be sensed by mobile computing device 108 as noted below. Custom instructions 212 can also include a dynamic adjustment mechanism. This mechanism can indicate, without further instructions from an entity associated with the instructions (e.g., medical institution 102), to alter times or situations responsive to previously set thresholds for a result of one of the monitoring acts. Thus, if person 106's temperature appears to be rising slightly, but not yet enough to confirm probable infection, the frequency of tests can be increased.

In some cases monitoring module 210 may include a dynamic warning mechanism set by medical institution 102, which can also be acted upon without further instruction from medical institution 102. This permits a flexible and immediate responsiveness to medical changes, such as a temperature differential of approximately 0.5° F. or 0.3° C.

Generally, monitoring module 210 is capable of prompting a person to initiated use of an in-ear device 104 based on prescribed times or situations. Monitoring module 210 may also or instead cause in-ear device 104 to perform the prescribed monitoring acts and then receive, store, and transmit the results. Monitoring module 210 may wait to transmit the results until a temperature differential meets some threshold, such as 0.25° F. or 0.2° C., or simply transmit after some duration of time or number of tests have been performed.

Mobile computing device 108 may also include or have access to passive sensors to determine if a situation is occurring, such as person 106 lying down to sleep, for example. Passive sensors can include an accelerometer that measures movement of mobile computing device 108, and thus indirectly movement of person 106, a touch sensor of a display screen capable of measuring person 106's skin temperature, capacitance, and/or conductivity, barometric sensors, light sensors, microphones, and radar sensors capable of passively sensing person 106's skin temperature, skeletal movement, and heart rate, to name but a few. While these measurements may not be sufficiently accurate or precise (e.g., repeatable) to measure small temperature differentials, they can be used to determine situations during which testing with in-ear device 104 is desired.

Monitoring module 210 may also use data associated with person 106 to determine when some situation is occurring, such as a global position through GPS, cellular, and/or local-area networks (LANs), thereby indicating that person 106 is out to dinner, walking along a street, driving, at work, at home, and so forth. Person-associated data may also include person 106's calendar or other personal information, and thus person 106's activities for various times of day, such as situations of person 106 being at work, at high activity, asleep, or in a particular location. Thus, monitoring module 210 is capable of determining, through use of passive sensors or person-associated data, that a particular situation is occurring. After the determination, monitoring module 210 may then prompt the person to use in-ear device 104.

Figure 3:
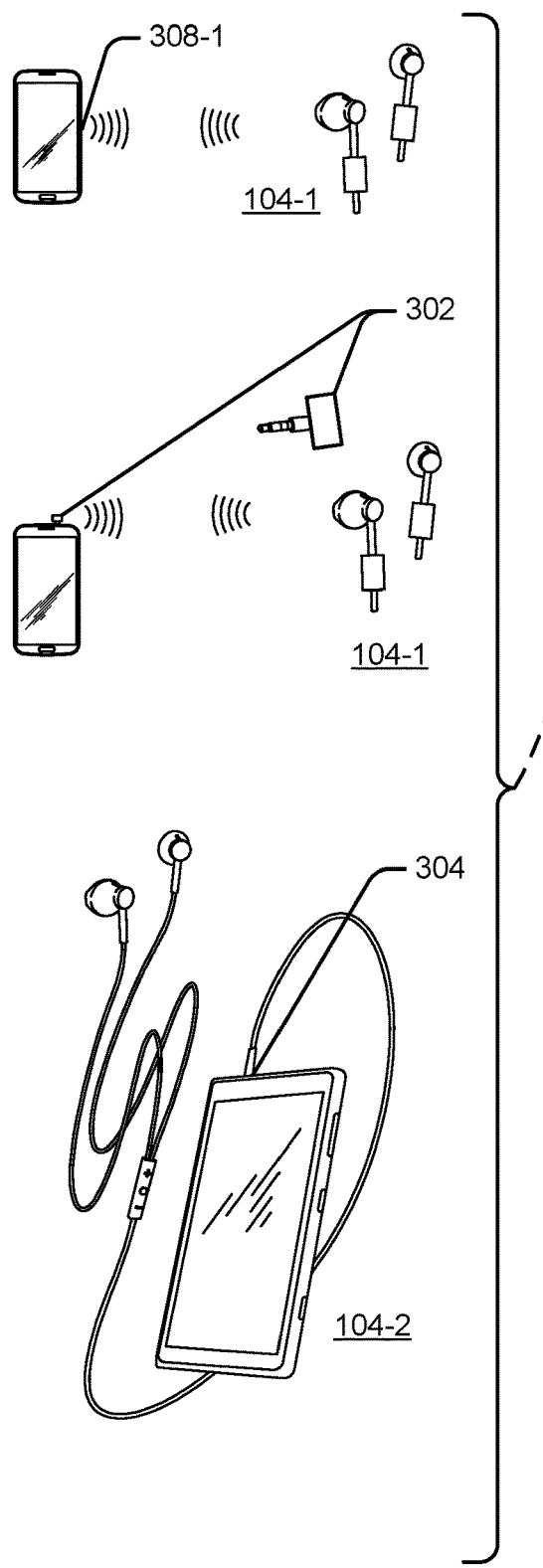
FIG. 3 illustrates an example in-ear health-monitoring and audio device of FIG. 1.

Consider, in more detail, in-ear device 104, examples of which are illustrated in FIG. 3. In-ear device 104 can be one in which many persons are familiar, offering pause, play, and volume controls (e.g., through hardware or contact switches), and in a form factor to which they are comfortable. In-ear device 104 can include wireless or wired devices, here illustrated with a wireless in-ear device 104-1 with and without a wireless audio plug 302 and a wired in-ear device 104-2 with wired audio plug 304. Note that wireless in-ear device 104-1 may use wireless communications through a wireless transceiver 306 to communicate with other devices through network 110 in well-known manners for wireless communication. In one example case, wireless audio plug 302 is included with wireless in-ear device 104-1, which can attach to a port (e.g., mini-USB or audio socket) of mobile computing device 108. In the wireless or wired cases, in-ear device 104 is capable of communicating with some external device, such mobile computing device 108.

In-ear device 104 also includes speaker 308 and temperature sensor 310. Speaker 308 is capable of rendering audio content, and may be one or more of various types of devices capable of producing sounds, such as an electroacoustic transducer that converts electrical signals to sound. In more detail, speaker 308 is configured to receive audio content from a mobile computing device. This can be through wireless audio plug 302 or wired audio plug 304. In the wired case, audio socket 218 (or USB, etc.) of mobile computing device 108, in electrical connection with wired audio plug 304, provides audio content. This audio content can then be presented, e.g., rendered, by speaker 308 so that person 106 can hear the content. The audio content may include any suitable type of content, such as audio of a phone call or entertainment content. The entertainment content can include any of various content that person 106 would like to hear, such as news, podcasts, media programs, audio books, and music.

Temperature sensor 310 is capable of sensing a temperature of a human auditory canal or tympanic membrane, such as that of person 106. Temperature sensor 310 may include a thermistor, and may include multiple temperatures sensors. Multiple temperature sensors permit a gradient across the temperature sensors, which enables estimation of an internal self-heating measurement of in-ear device 104. This can be useful in shortening a temperature-equalization period for in-ear device 104, which is described in detail later below. Multiple temperature sensors may also improve consistency in measured temperature where in-ear device 104 does not fully reach a stabilized, non-transient temperature equilibrium with person 106's inner-ear temperature.

Generally, reliability and consistency of measurement for temperature-sensing device can be improved by giving the device sufficient time to equilibrate with the object being measured. This permits the sensor to come to a relatively constant resistance through a lateral thermal diffusion time having been met or succeeded. Many conventional temperature-sensing devices used to measure people's temperature are still on a transient curve when taking a temperature measurement—these conventional devices are trying to estimate a steady state rather than being at that steady state. In contrast, in-ear device 104 can be at the steady state through overcoming a temperature-equilibrium period, whether through time in a person's auditory canal or through aid of a self-heating device as described in greater detail below.

In-ear device 104 also includes one or more of a hardware circuit 312, System-on-Chip 314, and/or computer processors 316 and computer-readable storage media 318. One or more of these is capable, through hardware, hardware in combination with software or firmware, or software, of managing speaker 308, temperature sensor 310, and receiving and sending data, such as audio signals and temperature readings. These capabilities are illustrated with sensor manager 320, shown as computer-executable instructions that computer processors 316 may execute, though these may also or instead, alone or in combination, be performed by hardware circuit 312 or firmware on SoC 314.

In more detail, sensor manager 320 is configured to communicate data with a mobile computing device. This can be through wireless audio plug 302 or wired audio plug 304. In the wired case, audio socket 218 (or USB, etc.) of mobile computing device 108, in electrical connection with wired audio plug 304, communicates data and other instructions. Manager 320 is also configured to sense a temperature of person 106's auditory canal or tympanic membrane by using or causing temperature sensor 310 to read a current temperature. With the resulting sensor data for the temperature reading, manager 320 can provide the sensor data through wired audio plug 304 and to audio socket 218 of mobile computing device 108.

Figure 4:
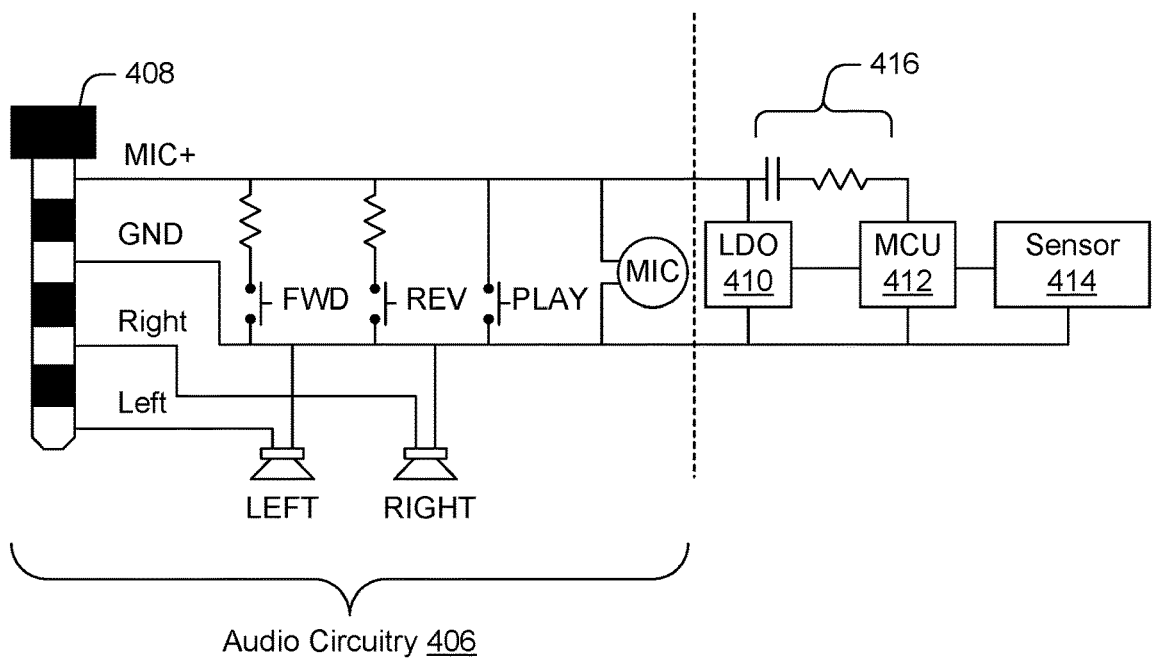
FIG. 4 illustrates example active and passive hardware circuitry for in-ear health-monitoring and audio devices of FIGS. 1 and 3.
Figure 4:
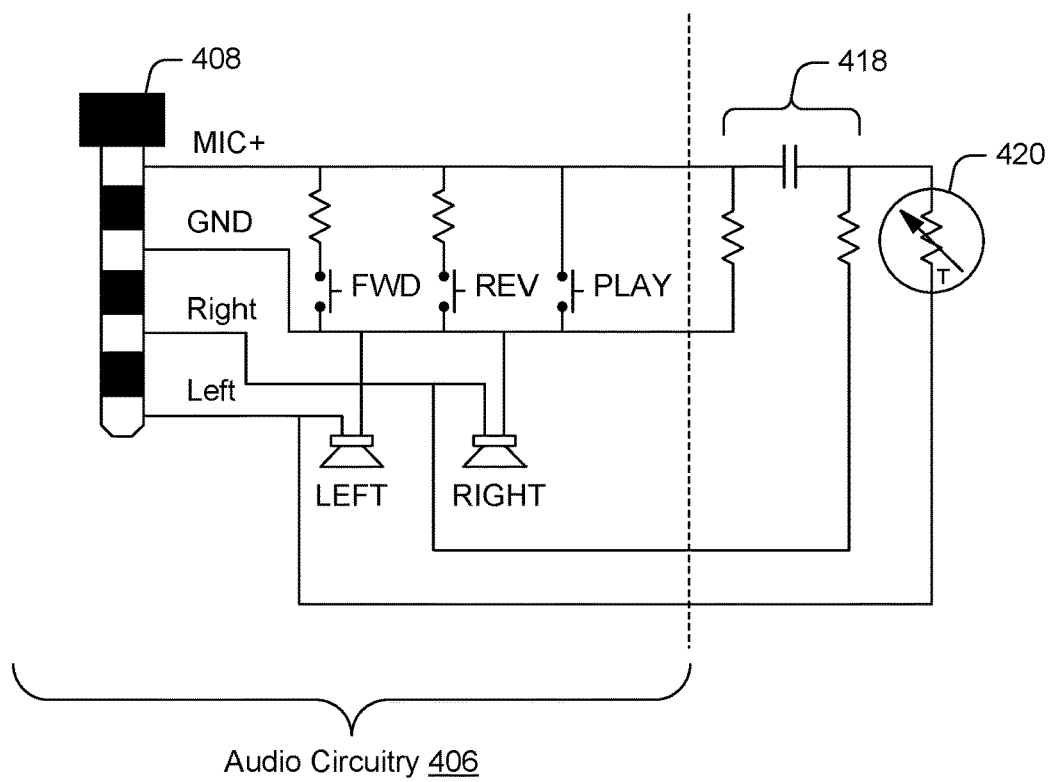

By way of two example configurations of hardware circuit 312, consider FIG. 4, which shows active hardware circuitry 402 (active circuitry 402) and passive hardware circuitry 404 (passive circuitry 404). Turning first to active circuitry 402, audio circuitry 406 may be implemented to provide standard audio functionality associated with an in-ear audio device. In this particular example, audio circuitry 406 interfaces via audio plug 408 (e.g., 4 pin 3.5 mm audio jack) to provide one channel of stereo audio output per in-ear audio device (e.g., speaker 308), such as a left audio channel for one earbud and a right audio channel for another earbud. Alternately, when implemented through a single in-ear device, the left and right stereo channels may be combined as mono audio so as not to lose a channel specific portion of the audio content.

Additionally, audio circuitry 406 may include a microphone to receive sound (e.g., voice calls or recordings) and hardware switches that enable remote control of playback functionalities a host device (e.g., mobile computing device 108). As shown in FIG. 4, these playback functionalities include fast-forward (FWD), reverse (REV), and play (or pause) for controlling the selection or rendering of audio content by the host device. The hardware switches may be implemented directly on in-ear device 104 or, in the case of wired implementations, a cord or wiring harness associated therewith (e.g., a snake-bump).

Active circuitry 402 also includes low-dropout regulator 410 (LDO 410), microcontroller unit 412, and temperature sensor 414 (sensor 414). LDO 410 can be configured to power components of active circuitry from bias current provided by an audio socket of mobile computing device 108. MCU 412, which is powered by LDO 410, is configured to measure a temperature of a human auditory canal or tympanic membrane via sensor 414, which may be implemented as temperature sensor 310 as described with reference to FIG. 3. MCU 412 can communicate data with mobile computing device 108 by encoding or modulating data through a microphone signal line. In this particular example, active circuitry 402 also includes DC blocking circuit 416 to block bias current on the microphone signal line and enable MCU 412 to transmit data to mobile computing device 108. Once received through the microphone signal line, mobile computing device 108 can then decode the data provided by MCU 412, such as temperature data, self-heating information, and the like. The data transmitted via the microphone signal line may be AC balanced and self-clocking, such as through the use of Manchester encoding or a similar scheme. Alternately or additionally, the data may be modulated or encoded on a microphone signal line so that it can be made inconspicuous to normal microphone usage. The encoded signal can be hidden by using inaudible signal modulation (frequency band or amplitude), low-level pseudo-random noise modulation, or simulating ambient noise (e.g., wind noise).

For example, in cases of wired in-ear devices, sensor data can be provided through an analog signal returned to mobile computing device 108 over a microphone input-capable element of audio socket 218. Note further than in this wired case, where wired audio plug 304 communicates through audio socket 218, in-ear device 104 may forgo use of a power element, such as a battery, within in-ear device 104. In this case, in-ear device 104 is powered by bias current provided by mobile computing device 108 through the wires from wired audio plug 304 to in-ear device 104.

In other embodiments, active circuitry 402 may communicate bi-directionally with the mobile computing device 108 using the microphone signal line in combination with one or both of the stereo audio signals. Additionally, the data may be modulated or encoded on the stereo audio signals so that it can be made inconspicuous to normal headphone usage, such as through the use of inaudible signal modulation, data encoded as pseudorandom noise, and the like. Data communicated by active circuitry 402 may also be configured to enable other various functionalities of in-ear device 104, such as calibration, manufacturing test, firmware updates, and the like.

Various techniques can be applied to the measurement of the passive temperature sensitive element in order to improve signal-to-noise ratios and reject interfering signals. One example is the use of discrete tones at an integer sub-divisor of audio sample rates. This allows use of a single frequency discrete cosine transform to encode and extract the signal without windowing artifacts while providing rejection of other frequencies that may contain noise or interference signals. Further, measurements can be made at multiple discrete frequencies to improve the signal-to-noise ratio as well as reject interfering signals, and in some cases perform a frequency chirp to measure the complete frequency dependent transfer function. These encoding or extraction techniques may be implemented by components or either or both of in-ear device 104 for the case of active circuitry 402 and mobile computing device 108 for the case of passive circuitry 404 to improve measurement integrity.

Passive circuitry 404 also includes audio circuitry 406, which may be implemented as described with reference to active circuitry 402. Passive circuitry 404 includes a resistor-capacitor network 418 (RC network 418) and thermistor 420, which are powered by the stereo audio signals of the left and right channels of audio circuitry 406. Thermistor 420 is configured to enable temperature measurements of a human auditory canal or tympanic membrane by providing or altering an analog signal returned to mobile computing device 108 via the microphone signal line. Although described here with reference to a thermistor, passive circuitry may be implemented using any suitable temperature sensitive element(s).

In at least some embodiments, the stereo audio signals are used as an excitation source for thermistor 420, which modulates a returning signal with temperature information for decoding by mobile device 108. In some cases, temperature measurements are performed during playback or rendering of audio content, such that audio signals associated with the content provide excitation for passive circuitry 404. Alternatively, an encoded excitation can be superimposed at an inaudible level relative to the audio content but effective to cause passive circuitry to provide a signal on the microphone signal line that can be decoded by mobile computing device 108. Alternately, when a signal level provided by passive circuitry is insufficient over a period of time, the temperature measurements may performed during a pause in audio playback effective to increase a quality of the signal provided.

In some embodiments, passive circuitry 404 enables temperature measurements to be performed through the use of transfer functions. For example, a frequency-dependent transfer function can be measured from audio output (e.g., right and/or left audio channels) to the microphone signal line, such as at the input of audio socket 218. Through use of various correlation techniques, an input signal can be time and phase aligned to the audio output to provide a basis for the transfer function. A frequency dependent gain can then be analyzed along with a model of a temperature independent transfer function to estimate, based on signals provided by passive circuitry 404, a temperature in person 106's auditory canal.

Through hardware circuitry 312, components of in-ear device 104 may implement, in part or whole, various aspects of in-ear health monitoring, such as measuring temperature of a human auditory canal or tympanic membrane. In at least some embodiments, sensor manager 320, whether operating as computer-readable instructions on CRM 318 or hardware circuit 312 and/or SoC 314, can perform temperature sensing during a pause in the audio presentation by speaker 308 or simultaneous with audio presentation by speaker 308 using temperature sensor 310.

As noted in part, CRM 318 includes sensor manager 320, which is capable of receiving instructions regarding when or how to sense person 106's temperature. These custom instructions may indicate when, though they may also be responsive to a user's interaction (e.g., the user is prompted by mobile computing device 108 rather than in-ear device 104). Responsive to interaction or instruction, sensor manager 320 causes temperature sensor 310 to sense person 106's temperature and then provides the result (e.g., results 216 to mobile computing device 108).

Providing results 216 can be performed in multiple different manners. In the wired case, sensor data can be provided through an analog signal returned to mobile computing device 108 over a microphone input-capable element of audio socket 218. Note further than in this wired case where wired audio plug 304 communicates through audio socket 218, in-ear device 104 may forgo use of a power element, such as a battery, within in-ear device 104. In this case, in-ear device 104 is powered by a bias current provided by mobile computing device 108 through the wires from wired audio plug 304 to in-ear device 104.

In-ear device 104 may also include a self-heating element 322. This self-heating element is capable of heating in-ear device 104 to a device temperature near to, but below an expected temperature of the human auditory canal or tympanic membrane, such as 92° F. Note that speaker 308 can be used as a self-heating element instead or in addition through electric signals exciting the structure of speaker 308, whether in an audible or in-audible range of sound.

Sensor manager 320 can also estimate self-heating of in-ear device 104. This estimation of self-heating can be performed through a model of electro-mechanical losses for speaker 308; such losses can be affected by a temperature of speaker 308. Note that a thermal model estimating an impact on temperature sensor 310 may also be used.

In some cases aspects common to audio socket 218 of mobile computing device 108 can be used, this can aid in lowering costs of in-ear device 104 to maintain is broad applicability in a medical crisis. Many audio sockets of mobile devices are capable of receiving a microphone signal. Using this capability, hardware circuitry 312 receives sensor data through wired audio plug 304 as an encoded signal on the microphone signal. Monitoring module 210 is then capable of decoding the encoded signal. This signal can be superimposed on an encoded excitation source at an inaudible level.

These and other capabilities, as well as ways in which entities of FIGS. 1-4 act and interact, are set forth in greater detail below. These entities may be further divided, combined, and so on. The environment 100 of FIG. 1 and the detailed illustrations of FIGS. 2-4 illustrate some of many possible environments capable of employing the described techniques.

Example Method

Figure 5:
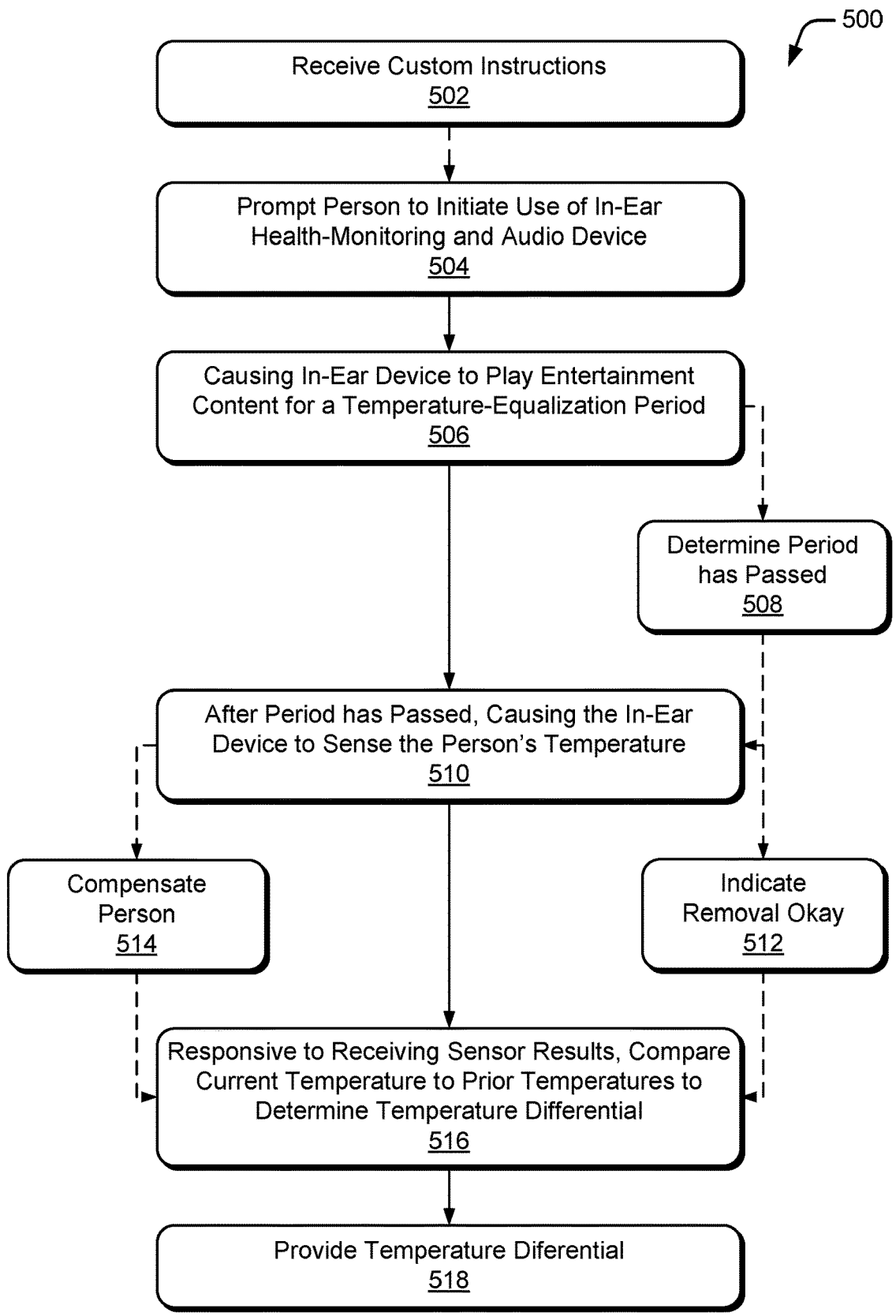
FIG. 5 illustrates a method enabling or using in-ear health monitoring.

FIG. 5 depicts a method enabling or using in-ear health monitoring. This method is shown as a set of blocks that specify operations performed but are not necessarily limited to the order or combinations shown for performing the operations by the respective blocks. In portions of the following discussion reference may be made to environment 100 of FIG. 1 and entities detailed in FIGS. 2-4, reference to which is made for example only. The techniques are not limited to performance by one entity or multiple entities operating on one device.

Optionally, at 502, custom instructions are received by a mobile computing device. As noted, these custom instructions can be created by a health professional, such as a medical doctor or disease-control institution. These custom instructions may include situations or times at which to monitor a person's health that are tailored to the person or disease, though such custom instructions are not required.

An indicator can be received by mobile computing device 108 when communication is established with in-ear device 104, such as prior to operations 502 or 504. Consider, for example, a case where thousands of in-ear devices 104 are passed out after a possible contamination. Person 106 may plug in the wired version into her smartphone 108-2. On plugging it in, in-ear device 104 may indicate to smartphone 108-2 a universal resource locator (URL) at which to download monitoring module 210 of FIG. 2. In other cases, in-ear device 104 may be tagged or imprinted with a quick response (QR) code that facilitates downloading of monitoring module 210 by smartphone 108-2. This is not required, but can improve ease of use for users. Alternatively, instructions can be provided with in-ear device 104, such as from a doctor or in a brochure packaged with in-ear device 104. These instructions can indicate how to download an application (an "App", here monitoring module 210). If provided by a particular medical doctor and for a particular person or disease custom instructions 212 can be downloaded by person 106 or the medical professional's request.

For this example, however, person 106 plugs in in-ear device 104 to her smartphone 108-2, which then uses the URL from CRM 318 or SoC 314 to download monitoring module 210. Assume at this particular point, that user interface 214 of monitoring module 210 then presents a list of selectable options for person 106 to select, such as:

Please indicate infectious disease: Ebola, Smallpox, Yellow Fever, Tuberculosis, Measles, Cholera, Malaria, Spanish Flu, Meningococcal Meningitis, Severe Acute Respiratory Syndrome, Bubonic Plague, Whooping Cough, Avian Flu, H1N1 Influenza, Syphilis, Marburg, Anthrax, Rabies, MRSA, or Other.

After selecting the disease, monitoring module 210 follows instructions tailored to that disease. This tailoring may include how and when in-ear device 104 is used and a temperature differential that indicates possible infection. These instructions may also customize use of user interface 214 such that the interface prompts person 106 responsive to a temperature differential indicating possible infection with questions about other symptoms common to the disease selected.

At 504, a user is prompted to initiate use of an in-ear health-monitoring and audio device. This prompting can be in various manners common to interfaces of mobile devices, such as shaking, sounds, alarms, content displayed, and so forth. In some cases, an external source may prompt the user to initiate use of the device, such as an incoming call, text messages, or media message received from a health provider, health facility, or the like.

Figure 6:
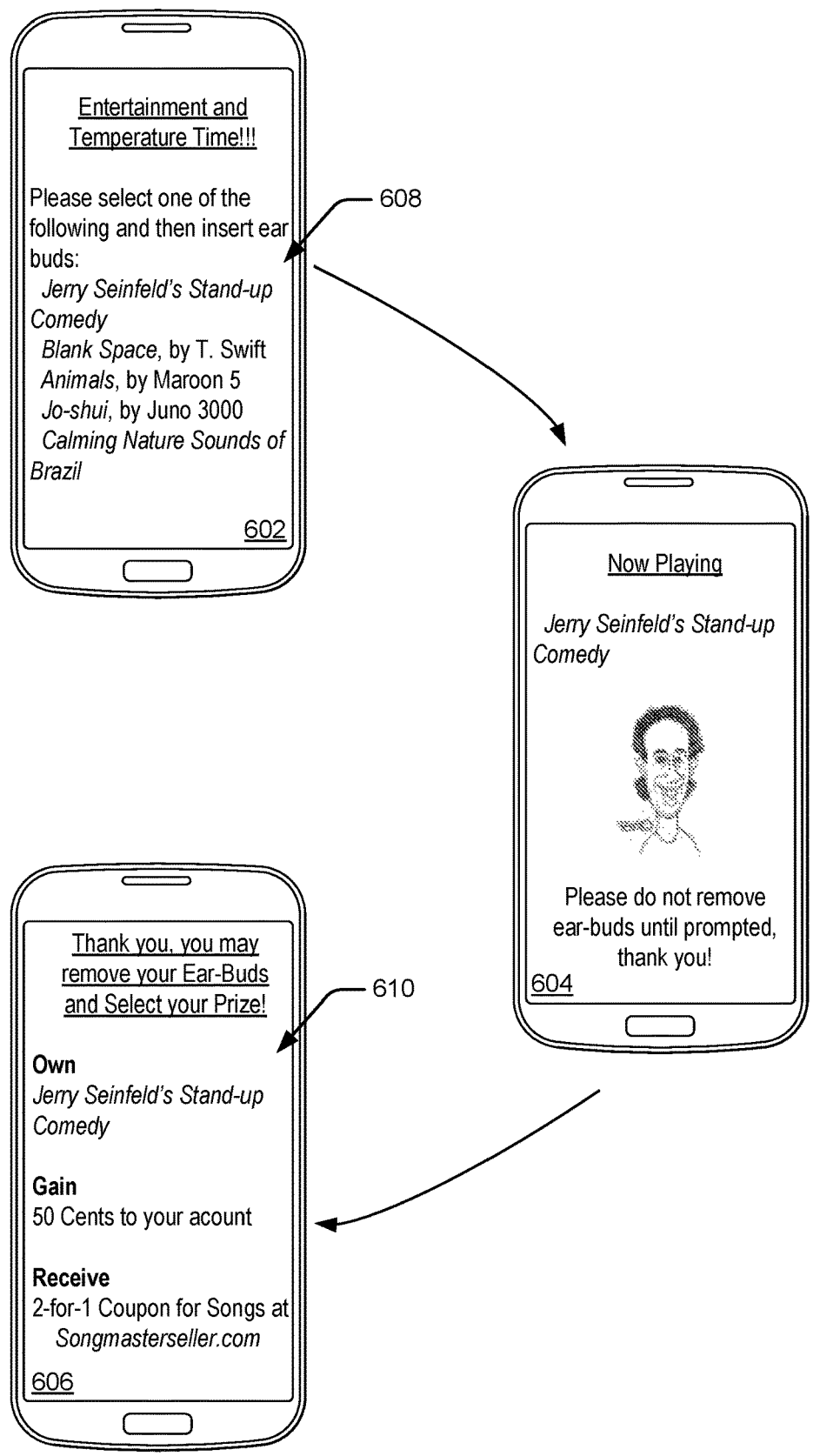
FIG. 6 illustrates example user interface displays, including a prompt display, an audio presentation display, and a temperature-sensing completion and compensation display.

Continuing the ongoing example, consider FIG. 6, which illustrates three example user interface displays: prompt display 602, audio presentation display 604, and temperature-sensing completion and compensation display 606. Prompt display 602 prompts person 106 to put in-ear device 104 in her ear canals. To encourage use of in-ear device 104 and use for a time period sufficient to accurately measure person 106's temperature, monitoring module 210 may present a list of selectable entertainment content 608. These selectable entertainment content 608 can be new content that is likely to be desirable to person 106 or old content known to be favored by person 106, or, if information about person 106 is not known, content likely to be favored by persons in the country, location, culture, age, or sex of the person, to name a few (e.g., Top 40 songs in China, one of which is Jo-shui, by Juno 3000 for 2015). Each of these selectable entertainment content 608 can be of temporal length sufficient to equilibrate in-ear device 104's temperature with that of person 106's auditory canal, though this is not strictly required. Here assume that person 106 puts in-ear device 104 into both of her auditory canals and then selects to hear comedy content, Jerry Seinfeld's Stand-Up Comedy.

At 506, the in-ear device is caused to render audio content for a temperature-equalization period. In some cases, this may include causing the playback of entertainment content or presenting audio content of an incoming call or received multimedia message. A duration of the temperature-equalization period can be shortened by self-heating, as noted above. This period can also be a strict equalization such that temperature sensor 310 is within 0.1, 0.2, or 0.3 degrees (Fahrenheit or Celsius) of the auditory canal or tympanic membrane. This period, however, may instead be one in which temperature is sufficiently equalized for temperature measurements to be consistent to within 0.1 degrees, though the accuracy of these measurements need not be 0.1 degrees. Thus, equalization can be as little as 10 degrees, for example, between in-ear device 104 and person 106's auditory canal, as temperature sensor 310 may still be able to consistently measure person 106's temperature. As noted, a temperature reading need not be accurate though it does have to be consistent to within the range at which an infection is detected, such as 0.1, 0.3, 0.5, or 1.0 degrees (Fahrenheit or Celsius).

Optionally, at 508, a determination that the temperature-equalization period has passed is made rather than simply performing the sensing responsive to the period passing. Various manners of determination can be made, such as using multiple temperature sensors as noted above, or determining that a thermistor's temperature reading has equalized based on data received from in-ear device 104, or through measuring resistance of speaker 308, also as described above.

At 510, after the temperature-equalization period has passed, the in-ear device is caused to sense the person's temperature. This can be performed during rendering of audio content (e.g., play of entertainment content) or after the rendering is over, as noted above. Here assume that monitoring module 210 or sensor manager 320 determines that the temperature-equalization period has passed, and then, while play of Jerry Seinfeld's Stand-Up Comedy continues, one of both of the module or manager causes temperature sensor 310 to sense person 106's temperature. In cases where the temperature is sensed after play is over, a prompt by user interface 214 can indicate that in-ear device 104 should not be removed yet, such as a quick audio of "Please wait to remove ear-buds until you hear the beep" or a display and so forth.

Optionally, at 512, responsive to receiving sensor results, the in-ear device is caused to indicate to the person that the in-ear device can be removed (e.g., it is "okay"). This is optional though, in cases where an audio prompt is used to remind the person not to remove the in-ear device, some audio indication can be helpful in giving the temperature sensor adequate time to perform the measurement.

As another option, at 514, the person can be compensated for use of the in-ear device. Generally, this compensation can be anything that motivates the person to use the in-ear device when prompted. Compensation can include addition of content to a mobile device's audio or audio-visual library, such as a book on tap, a podcast, a song (with or without a music video), a drama or comedy program, an e-book (audio or not), and so forth. Compensation may also include money, coupons, discounts, exclusive deals, and so forth. Continuing the ongoing example, temperature-sensing completion and compensation display 606 of FIG. 6 indicates both that in-ear device 104 can be removed as well as a list of selectable compensations 610. These compensations include ownership or license to use the entertainment content just enjoyed, 50 cents (USD) added to person 106's media-purchase account or bank account, or a coupon for two-for-one purchase of songs from a particular web-enable content provider. These are some of nearly limitless possibilities for compensation persons to use in-ear device 104.

At 516, responsive to receiving sensor results for the person's temperature, the person's temperature is compared to one or more prior person temperatures sensed by the in-ear health-monitoring and audio device. By so doing, a temperature differential for the person is determined. As noted in part, this temperature differential can be independent of an accuracy of the in-ear device but dependent on a precision (e.g., repeatability) of the in-ear device. Because of this, inaccurate but precise measurements over multiple iterations are acceptable for determining a temperature differential. Many people insert audio devices, such as in-ear device 104 in very similar if not nearly identical manners each time they do so. This may be due in part to comfort, but also in part to a desire to achieve a best audio reproduction or sound clarity. Many people, however, do not behave in this manner for other testing devices, which is but one of the many reasons why in-ear device 104 enables consistent temperature readings and accurate temperature differentials.

While determining a temperature differential for the person need not be accurate but does need a high-level of consistency, some physiological factors may affect whether or not a particular differential indicates a likely infection. Human beings have small temperature differences at particular times of the day or month that can affect this temperature differential. Examples include harmonic variations related to daily rhythms for the person, circadian rhythm, reproductive cycles, and situation in which the person is in. The situations can be compensated for by having the person take their temperature during same or similar situations in some cases. Even so, recognizing small temperature variations that are consistent for most people or the particular person (e.g., determined through a prior use where infection was not found), can be used to compensate the initial differential to provide the temperature differential used to determine infection.

At 518, the temperature differential is provided to an entity associated with the person, a mobile computing device associated with the person, or a medical person or institution. If this temperature differential indicates likely infection, the person may be given instructions on what to do, such as call the person's medical professional, or information can be provided to the person that is previously determined appropriate for the disease selected (if any), further testing can also be requested for the person, whether through in-ear device 104 or other manners, or an interface provided with symptoms associated with the disease so, based on selections from the person greater accuracy in the determination of the infection can be made.

As is readily apparent, the techniques permit varied and robust health monitoring during a person's real life, whether at particular times, situations, or in particular conditions. By so doing, the spread of infectious diseases can be reduced and a likelihood of a successful outcome for infected persons used the in-ear device can be increased. Note also some of the tangential potential benefits also of reducing stress on persons that may have been exposed by giving them health monitoring that provides an accurate temperature differential and thus potentially and earlier way to catch the disease, as well as lowering the stress on medical institutions during times at which they are very likely to be overwhelmed, such as during a local outbreak of an infectious disease.

Furthermore, through many iterations of many people using in-ear devices 104, better data can be found. This better data permits further refinement of what temperature differentials indicate infection and for which diseases, including rates at which these temperature differentials are found. Thus, while medical science may not now know if persons that have contract Ebola will have an increase in 0.5 degrees within 24 hours of possible infection and then 1.0 degree within 36 hours, and so forth along a curve of temperature-differential increases over time. But, through these devices and techniques, such information may be learned, thereby improving early detection and slowing spread of various infectious diseases.

The preceding discussion describes methods relating to in-ear health monitoring. Aspects of these methods may be implemented in hardware (e.g., fixed logic circuitry), firmware, software, manual processing, or any combination thereof. These techniques may be embodied on one or more of the entities shown in FIGS. 1-4, 6, and 7 (computing system 700 is described in FIG. 7 below), which may be further divided, combined, and so on. Thus, these figures illustrate some of the many possible systems or apparatuses capable of employing the described techniques. The entities of these figures generally represent software, firmware, hardware, whole devices or networks, or a combination thereof.

Example Computing System

Figure 7:
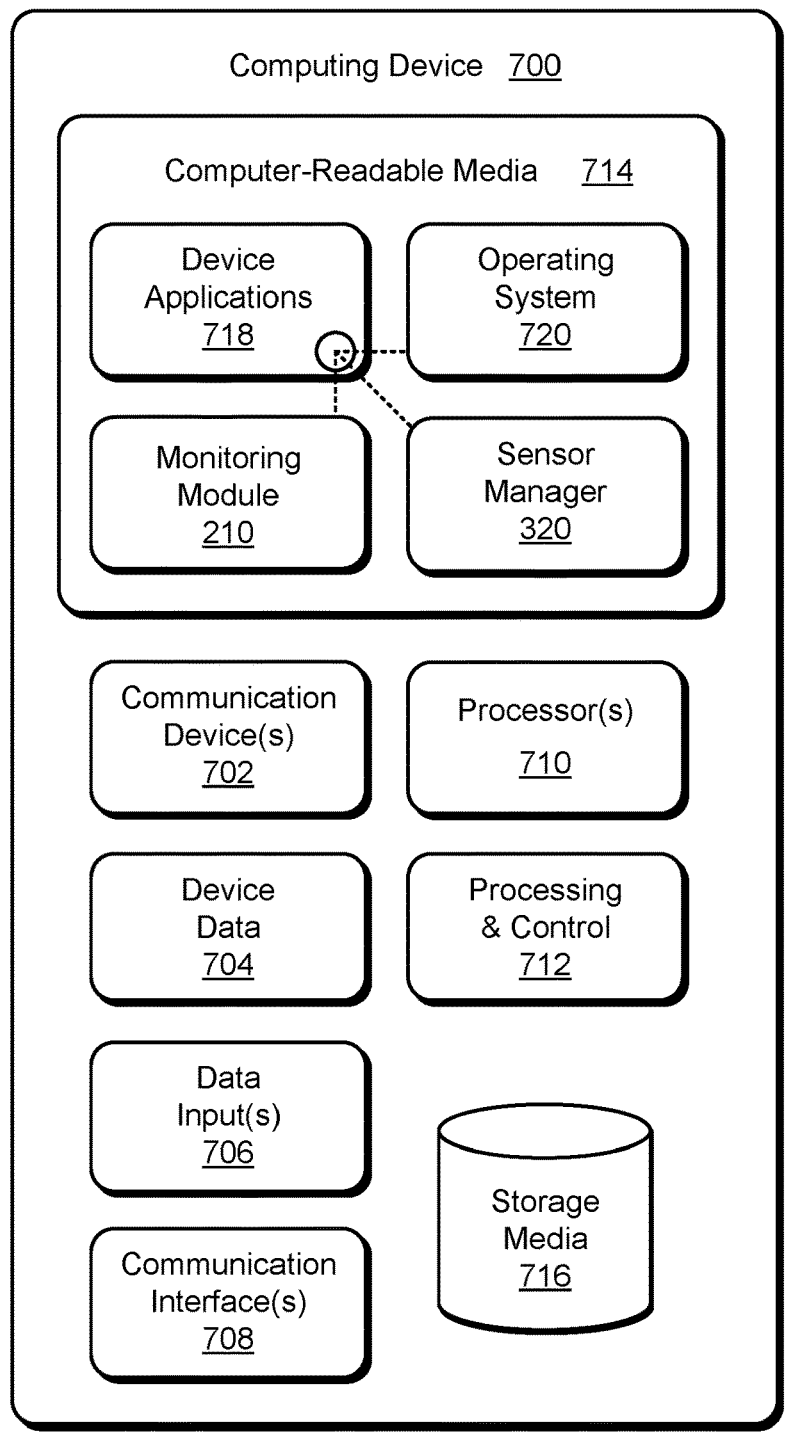
FIG. 7 illustrates an example device embodying, or in which techniques may be implemented that enable use of, in-ear health monitoring.

FIG. 7 illustrates various components of example computing system 700 that can be implemented as any type of client, server, and/or computing device as described with reference to the previous FIGS. 1-6 to implement in-ear health monitoring. In embodiments, computing system 700 can be implemented as one or a combination of a wired and/or wireless wearable device, health monitoring device, System-on-Chip (SoC), and/or as another type of device or portion thereof. Computing system 700 may also be associated with a user (e.g., a person) and/or an entity that operates the device such that a device describes logical devices that include users, software, firmware, and/or a combination of devices.

Computing system 700 includes communication devices 702 that enable wired and/or wireless communication of device data 704 (e.g., received data, data that is being received, data scheduled for broadcast, data packets of the data, etc.). Device data 704 or other device content can include configuration settings of the device, media content stored on the device, and/or information associated with a user of the device. Media content stored on computing system 700 can include any type of audio, video, and/or image data, including complex or detailed results of human-health-monitoring acts. Computing system 700 includes one or more data inputs 706 via which any type of data, media content, and/or inputs can be received, such as human utterances, user-selectable inputs (explicit or implicit), messages, music, television media content, recorded video content, and any other type of audio, video, and/or image data received from any content and/or data source.

Computing system 700 also includes communication interfaces 708, which can be implemented as any one or more of a serial and/or parallel interface, a wireless interface, any type of network interface, a modem, and as any other type of communication interface. Communication interfaces 708 provide connection and/or communication links between computing system 700 and a communication network by which other electronic, computing, and communication devices communicate data with computing system 700.

Computing system 700 includes one or more processors 710 (e.g., any of microprocessors, controllers, and the like), which process various computer-executable instructions to control the operation of computing system 700 and to enable techniques for, or in which can be embodied, in-ear health monitoring. Alternatively or in addition, computing system 700 can be implemented with any one or combination of hardware, firmware, or fixed logic circuitry that is implemented in connection with processing and control circuits which are generally identified at 712. Although not shown, computing system 700 can include a system bus or data transfer system that couples the various components within the device. A system bus can include any one or combination of different bus structures, such as a memory bus or memory controller, a peripheral bus, a universal serial bus, and/or a processor or local bus that utilizes any of a variety of bus architectures.

Computing system 700 also includes computer-readable media 714, such as one or more memory devices that enable persistent and/or non-transitory data storage (i.e., in contrast to mere signal transmission), examples of which include random access memory (RAM), non-volatile memory (e.g., any one or more of a read-only memory (ROM), flash memory, EPROM, EEPROM, etc.), and a disk storage device. A disk storage device may be implemented as any type of magnetic or optical storage device, such as a hard disk drive, a recordable and/or rewriteable compact disc (CD), any type of a digital versatile disc (DVD), and the like. Computing system 700 can also include a mass storage media device 716.

Computer-readable media 714 provides data storage mechanisms to store device data 704, as well as various device applications 718 and any other types of information and/or data related to operational aspects of computing system 700. For example, an operating system 720 can be maintained as a computer application with computer-readable media 714 and executed on processors 710. Device applications 718 may include a device manager, such as any form of a control application, software application, signal-processing and control module, code that is native to a particular device, a hardware abstraction layer for a particular device, and so on.

Device applications 718 also include any system components, modules, or managers to implement in-ear health monitoring. In this example, device applications 718 include monitoring module 210 or sensor manager 320.

Conclusion

Although embodiments of techniques using, and apparatuses for implementing, in-ear health monitoring have been described in language specific to features and/or methods, it is to be understood that the subject of the appended claims is not necessarily limited to the specific features or methods described. Rather, the specific features and methods are disclosed as example implementations of in-ear health monitoring.

What is claimed is:

1. An in-ear health-monitoring and audio device comprising:
  an audio plug configured to enable communication of audio content and temperature data with a port of a mobile computing device;
  a speaker configured to render the audio content into a human auditory canal for at least a temperature-equalization period;
  a temperature sensor; and
  hardware circuitry or a System-on-Chip (SoC) configured to:
    responsive to the speaker rendering the audio content for at least the temperature-equalization period, sense, the temperature of the human auditory canal via the temperature sensor; and
    provide the temperature to the port of the mobile computing device via the audio plug.

2. The in-ear health-monitoring and audio device of claim 1, wherein the hardware circuitry or SoC is further configured to determine that the temperature equalization period has passed based on the in-ear health-monitoring and audio device reaching a stabilized, non-transient temperature equilibrium with the human auditory canal.

3. The in-ear health-monitoring and audio device of claim 2, wherein:
the temperature sensor comprises a thermistor configured to perform multiple temperature measurements; and
the hardware circuitry or SOC is further configured to determine that the temperature-equalization period has passed based on the multiple temperature measurements equalizing.

4. The in-ear health-monitoring and audio device of claim 2, wherein the hardware circuitry or SOC is further configured to determine that the temperature-equalization period has passed based on electro-mechanical losses associated with the speaker.

5. The in-ear health-monitoring and audio device of claim 2, further comprising another temperature sensor,
wherein the hardware circuitry or SoC is further configured to determine that the completion of the temperature-equalization period has passed based on a gradient across the temperature sensor and the other temperature sensor.

6. The in-ear health-monitoring and audio device of claim 1, wherein the hardware or SoC is configured to:
determine a temperature differential based on a comparison of the temperature with one or more prior temperatures sensed via the temperature sensor; and
provide the temperature differential to the port of the mobile computing device via the audio plug.

7. The in-ear health-monitoring and audio device of claim 6, wherein:
the hardware circuitry or SoC is configured to encode the temperature differential on a microphone signal; and
the audio plug comprises a wired audio plug, the wired audio plug configured to provide the microphone signal to the port of the mobile computing device via a wire of the wired audio plug.

8. The in-ear health-monitoring and audio device of claim 7, wherein the hardware circuitry or SoC is configured to encode the temperature differential on the microphone signal using an inaudible signal modulation or a pseudo-random noise modulation.

9. The in-ear health-monitoring and audio device of claim 7, wherein the wired audio plug is configured to provide power to the hardware circuitry or SoC via a bias current provided from the port of the mobile computing device via the wire.

10. The in-ear health-monitoring and audio device of claim 1, further comprising a wireless transceiver, wherein:
the audio plug comprises a wireless audio plug; and
the wireless transceiver is configured to wirelessly communicate with the wireless audio plug to obtain the audio content from the port of the mobile computing device and provide the temperature to the port of the mobile computing device.

11. The in-ear health-monitoring and audio device of claim 1, further comprising a self-heating element configured to generate heat to shorten the temperature-equalization period.

12. The in-ear health-monitoring and audio device of claim 11, wherein the self-heating element includes the speaker, the speaker configured to generate the heat based on audible or in-audible electric signals exiting a structure of the speaker.

13. A system comprising:
an in-ear health-monitoring and audio device configured to:
render audio content into a human auditory canal for at least a temperature equalization period; and
responsive to rendering the audio content for at least the temperature-equalization period, sense a temperature of the human auditory canal; and
a monitoring module configured to:
provide the audio content to the in-ear health-monitoring and audio device; and
determine a temperature differential based on a comparison of the temperature with one or more prior temperatures sensed via the in-ear health monitoring and audio device.

14. The system of claim 13, wherein the monitoring module is configured to:
present a list of selectable audio content to a user, each of the selectable audio content having temporal lengths greater than or equal to the temperature equalization period; and
provide the audio content based on a chosen audio content that is selected from the list of selectable audio content.

15. The system of claim 13, wherein the monitoring module is configured to prompt a person to initiate use of the in-ear health-monitoring and audio device.

16. The system of claim 15, wherein the monitoring module is configured to:
prompt a user to select a disease; and
adjust a frequency at which the user is prompted and the temperature is sensed based on the selected disease to enable the temperature differential to indicate whether the user is infected with the selected disease.

17. The system of claim 15, wherein the monitoring module is configured to increase a frequency at which the user is prompted and the temperature is sensed based on the temperature differential indicating an increase in temperature.

18. The system of claim 13, wherein the in-ear health-monitoring and audio device is configured to:
sense the temperature during continued rendering of the audio content after the temperature-equalization period has passed; or
sense the temperature after the rendering of the audio content has ceased.

19. The system of claim 13, wherein the in-ear health-monitoring and audio device is configured to be coupled to the monitoring module via a wired interface or a wireless interface.

20. The system of claim 13, wherein the in-ear health-monitoring and audio device is configured to sense a temperature of a tympanic membrane within the human auditory canal.

\* \* \* \* \*